US009024140B2

(12) United States Patent
Bunn et al.

(10) Patent No.: US 9,024,140 B2
(45) Date of Patent: May 5, 2015

(54) METHODS AND COMPOSITIONS FOR PRODUCING PLANTS WITH ELEVATED BRIX

(75) Inventors: Teresa Beck Bunn, Woodland, CA (US); Anna Frampton, Friday Harbor, WA (US); Elaine Graham, Davis, CA (US); Joshua J. Lloyd, West Sacramento, CA (US)

(73) Assignee: Seminis Vegetable Seeds, Inc., Woodland, CA (US)

( * ) Notice: Subject to any disclaimer, the term of this patent is extended or adjusted under 35 U.S.C. 154(b) by 617 days.

(21) Appl. No.: 12/872,811

(22) Filed: Aug. 31, 2010
(Under 37 CFR 1.47)

(65) Prior Publication Data

US 2011/0283402 A1    Nov. 17, 2011

Related U.S. Application Data

(60) Provisional application No. 61/238,577, filed on Aug. 31, 2009.

(51) Int. Cl.
| | | |
|---|---|---|
| *A01H 5/00* | (2006.01) | |
| *A01H 5/10* | (2006.01) | |
| *C12Q 1/68* | (2006.01) | |
| *A01H 5/08* | (2006.01) | |

(52) U.S. Cl.
CPC ............... *C12Q 1/6895* (2013.01); *A01H 5/08* (2013.01); *C12Q 2600/13* (2013.01); *C12Q 2600/156* (2013.01)

(58) Field of Classification Search
None
See application file for complete search history.

(56) References Cited

FOREIGN PATENT DOCUMENTS

WO    WO 01/49105    7/2001

OTHER PUBLICATIONS

Yates et al (2004, Euphytica 135:283-296).*
Monforte et al., "Development of a set of near isogenic and backcross recombinant inbred lines containing most of the *Lycopersicon hirsutum* genome in a *L. esculentum* genetic background: A tool for gene mapping and gene discovery," Genome, 43(5):803-813, 2000.
GenBank Sequence AW648986.1, "EST327440 tomato germinating seedlings, TAMU *Solanum lycopersicum* cDNA clone cLEI6P5 5-, mRNA sequence", May 18, 2001.
Baxter et al., "Fruit Carbohydrate metabolism in an introgression line of Tomato with increased fruit soluble solids", *Plant Cell Physiol.*, 46(3):425-437, 2005.
Bernacchi et al., Advanced backcross QTL analysis in tomato. I. Identification of QTLs for traits of agronomic importance from *Lycopersicon hirsutum*, Theoretical and Applied Genetics, 97:381-397, 1998a.
Bernacchi et al., "Advanced backcross QTL analysis of tomato. II. Evaluation of near-isogenic lines carrying single-donor introgressions for desirable wild QTL-alleles derived from *Lycopersicon hirsutum* and *L. pimpinellifolium*", Theoretical and Applied Genetics, 97:170-180, 1998b.
Frary et al., "Fine mapping of quantitative trait loci for improved fruit characteristics from *Lycopersicon chmielewskii* chromosome 1", Genome, 46:235-243, 2003.
Fridman et al., "A recombination hotspot delimits a wild-species quantitative trait locus for tomato sugar content to 484 bp within an invertase gene", PNAS, 97(9):4718-4723, 2000.
Fulton et al., "QTL analysis of an advanced backcross of *Lycopersicon peruvianum* to the cultivated tomato and comparisons with QTLs found in other wild species", Theoretical Applied Genetics, 95:881-894, 1997.
Grandillo et al., "Advanced backcross QTL analysis: Results and perspectives", Proceedings of the International Congress "In the Wake of the Double Helix: From the Green Revolution to the Gene Revolution", Bologna, Italy, 27-31, pp. 115-132, 2003.
Malundo et al., "Flavor quality of fresh tomato (*Lycopersicon esculentum* Mill.) as affected by sugar and acid levels", Postharvest Biology and Technology, 6:103-110, 1995.
Monforte et al., Comparison of a set of allelic QTL-NILs for chromosome 4 of tomato: Deductions about natural variation and implications for germplasm utilization, TAG Theoretical and Applied Genetics, 102(4):572-590, 2001.
Paterson et al., "Fine mapping of quantitative trait loci using selected overlapping recombinant chromosomes, in an interspecies cross of tomato", Genetics, 124:735-742, Mar. 1990.
Tanksley and Nelson, "Advanced backcross QTL analysis: a method for the simultaneous discovery and transfer of valuable QTLs from unadapted germplasm into elite breeding lines", Theor Appl Genet, 92:191-203, 1996.
Tanksley et al., "High Density Molecular Linkage Maps of the Tomato and Potato Genomes", Genetics, 132:1141-1160, Dec. 1992.
Yates, et al., Comparative fine mapping of fruit quality QTLs on chromosome 4 introgressions derived from two wild tomato species, *Euphytica*,135(3):283-296, 2004.

* cited by examiner

*Primary Examiner* — Stuart F Baum
(74) *Attorney, Agent, or Firm* — Dentons US LLP; Alissa Eagle, Esq.

(57) ABSTRACT

The invention provides compositions and methods relating to the separation of elevated Brix from linked but undesirable agronomic traits among progeny with introgressions following a cross between *Lycopersicon esculentum* and *Lycopersicon hirsutum*. The invention further provides plants, plant parts, and seeds comprising such elevated Brix, which do not comprise alleles specifying undesirable agronomic traits that are genetically linked to the elevated Brix trait.

4 Claims, 7 Drawing Sheets

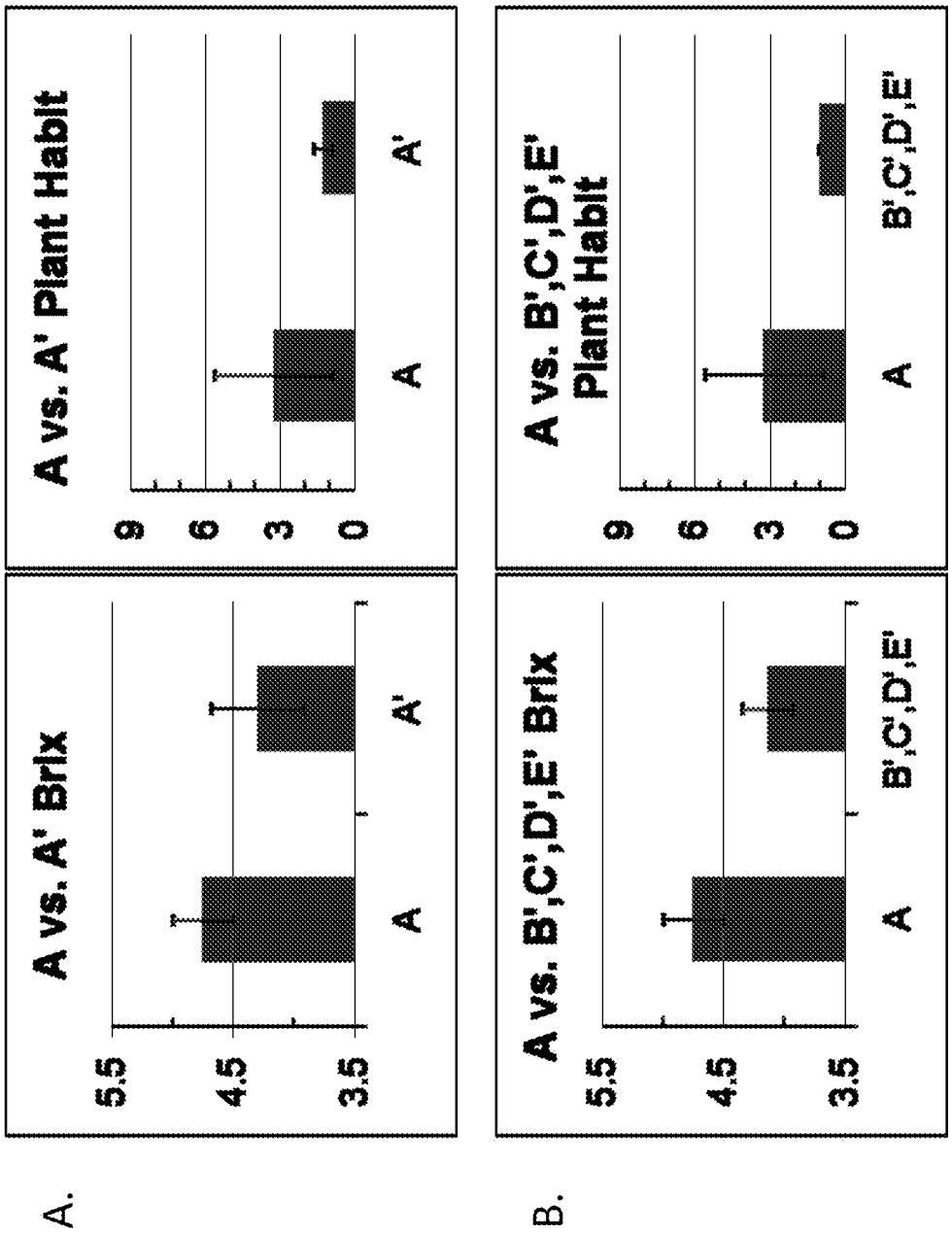
FIG. 2A-B

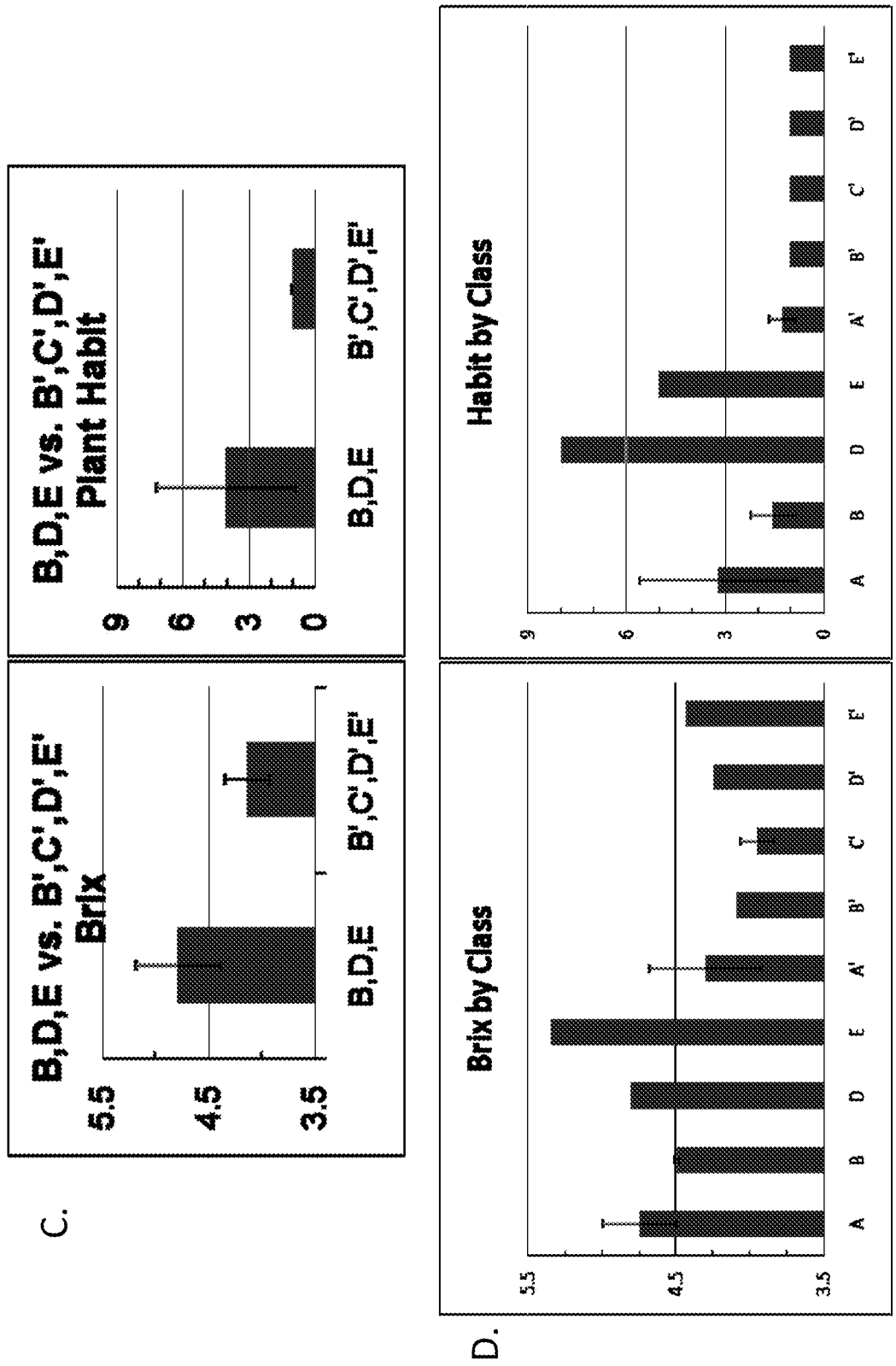
FIG. 2C-D

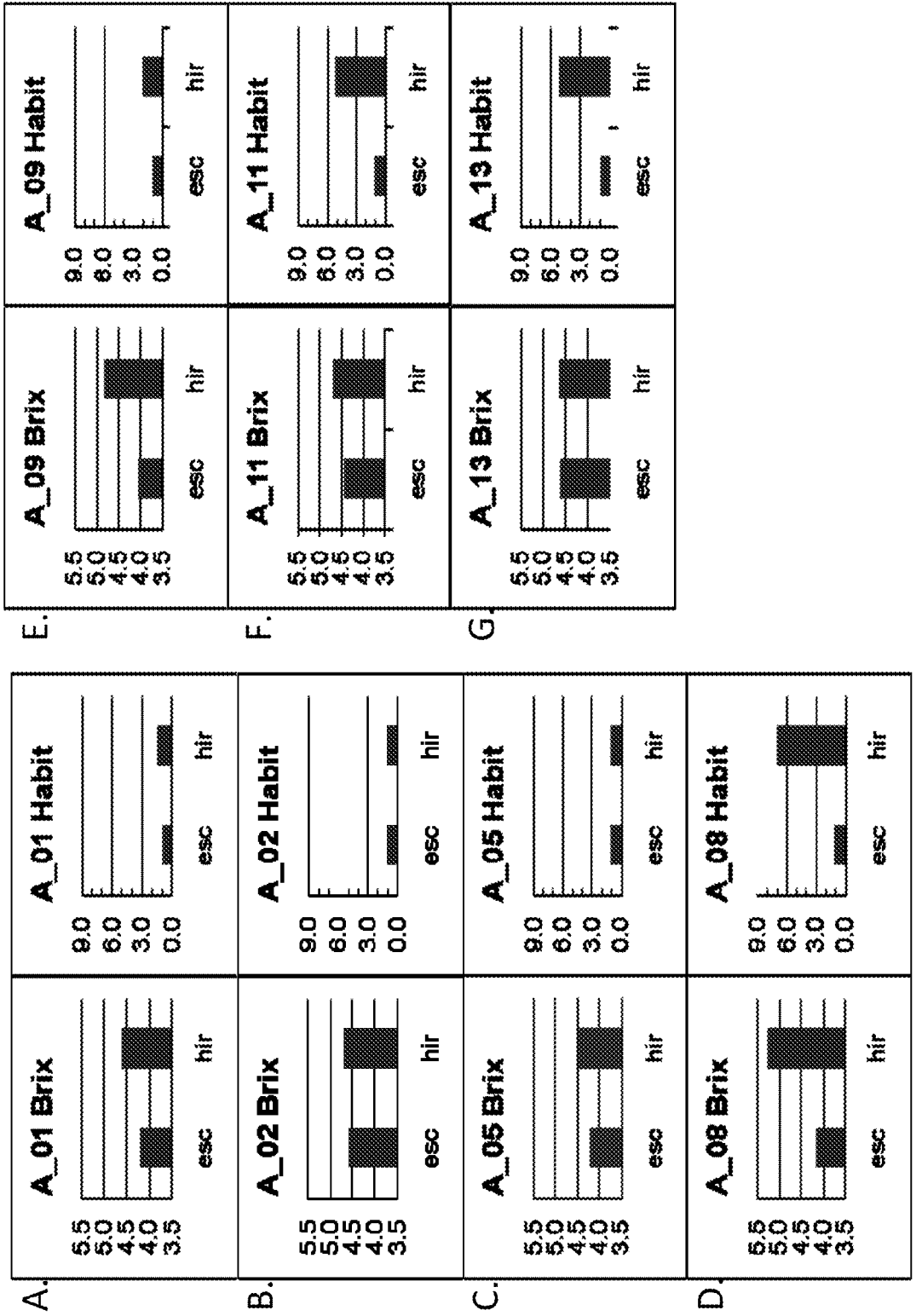
FIG. 3A-G

FIG. 4A-B
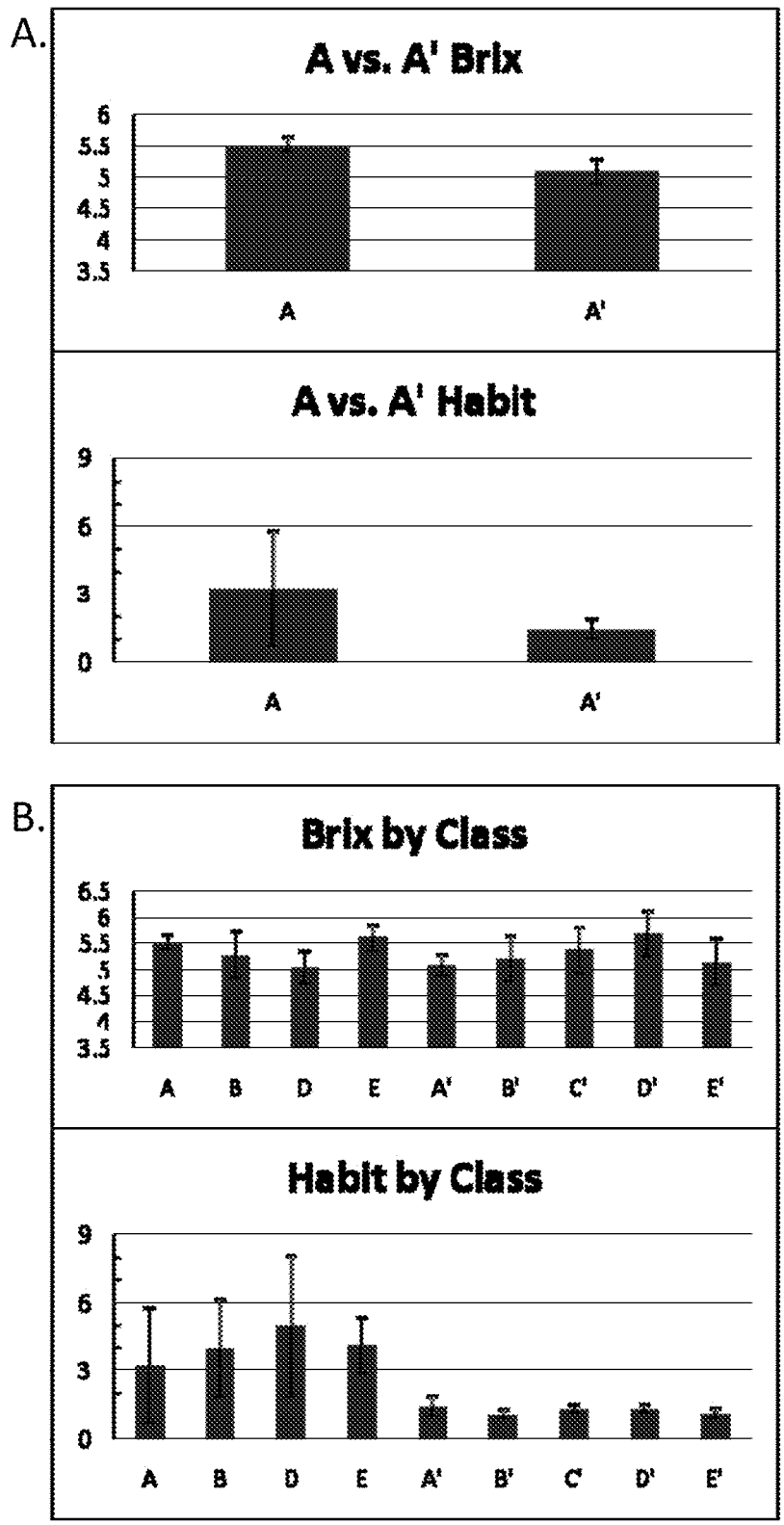

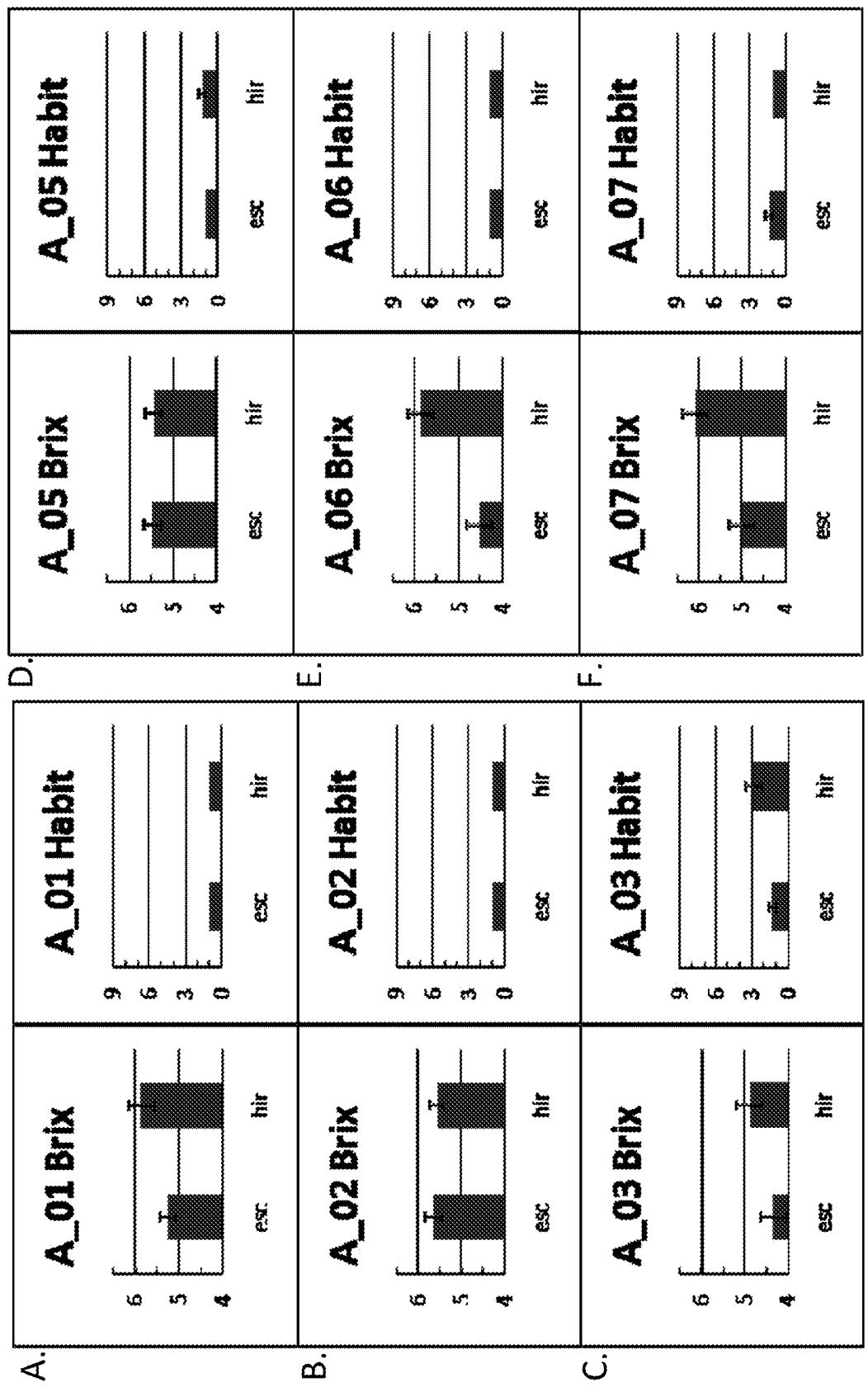
FIG. 5A-F

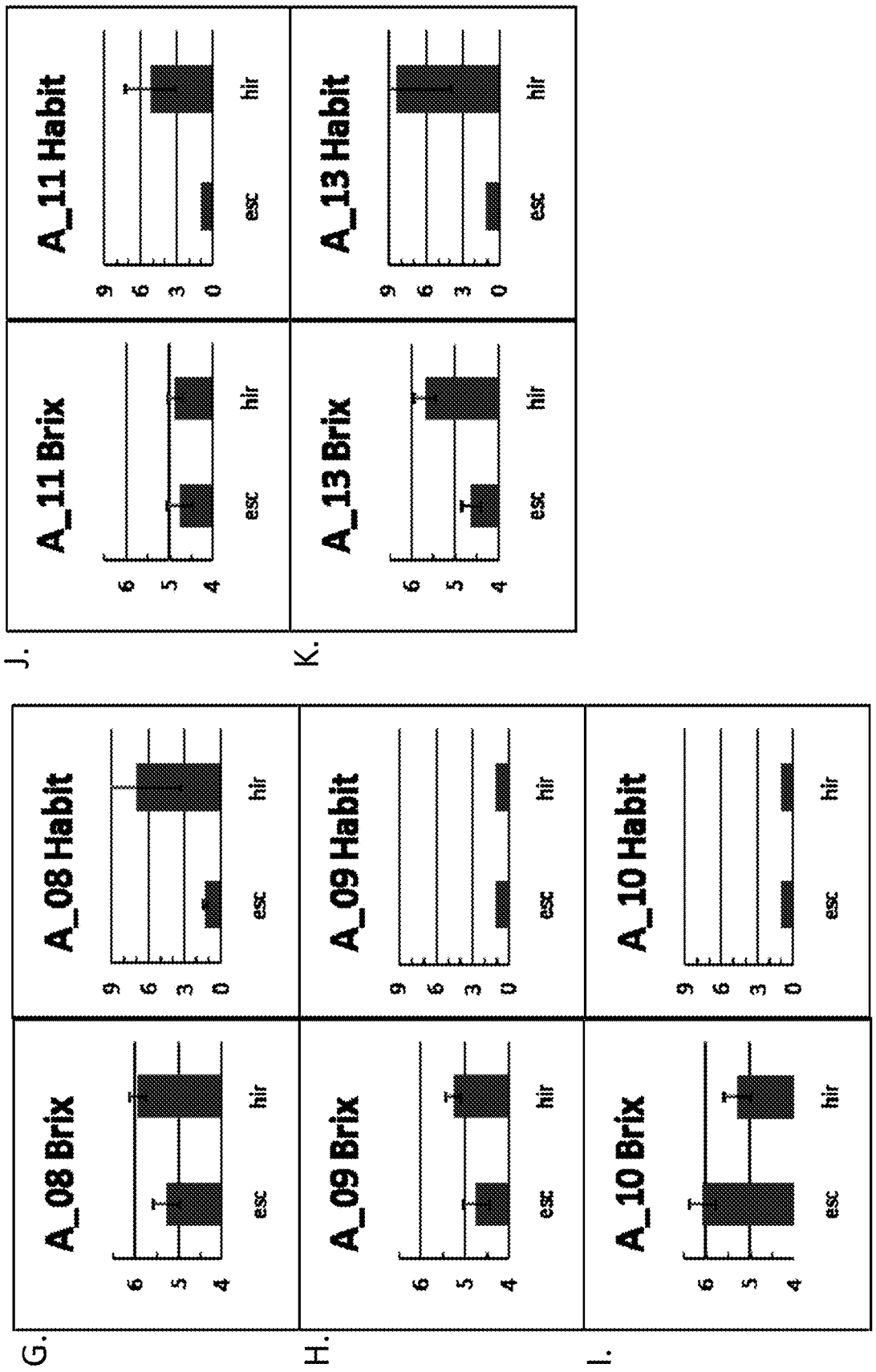
FIG. 5G-K

SEQUENCE LISTING

<160> NUMBER OF SEQ ID NOS: 64

<210> SEQ ID NO 1
<211> LENGTH: 30
<212> TYPE: DNA
<213> ORGANISM: Artificial Sequence
<220> FEATURE:
<223> OTHER INFORMATION: Primer

<400> SEQUENCE: 1
tgaacttgaa tctcctcttc attttgatga                                    30

<210> SEQ ID NO 2
<211> LENGTH: 27
<212> TYPE: DNA
<213> ORGANISM: Artificial Sequence
<220> FEATURE:
<223> OTHER INFORMATION: Primer

<400> SEQUENCE: 2
agttcttcac ctaagcttga ggatttt                                       27

<210> SEQ ID NO 3
<211> LENGTH: 18
<212> TYPE: DNA
<213> ORGANISM: Artificial Sequence
<220> FEATURE:
<223> OTHER INFORMATION: Probe

```
<400> SEQUENCE: 3
ctatggcttt aagcttag                                                    18

<210> SEQ ID NO 4
<211> LENGTH: 16
<212> TYPE: DNA
<213> ORGANISM: Artificial Sequence
<220> FEATURE:
<223> OTHER INFORMATION: Probe

<400> SEQUENCE: 4
atggctttga gcttag                                                      16

<210> SEQ ID NO 5
<211> LENGTH: 24
<212> TYPE: DNA
<213> ORGANISM: Artificial Sequence
<220> FEATURE:
<223> OTHER INFORMATION: Primer

<400> SEQUENCE: 5
tcatccaaac tctgctgaac atca                                             24

<210> SEQ ID NO 6
<211> LENGTH: 24
<212> TYPE: DNA
<213> ORGANISM: Artificial Sequence
<220> FEATURE:
<223> OTHER INFORMATION: Primer

<400> SEQUENCE: 6
atgttgatct ctttgcagta ggca                                             24

<210> SEQ ID NO 7
<211> LENGTH: 17
<212> TYPE: DNA
<213> ORGANISM: Artificial Sequence
<220> FEATURE:
<223> OTHER INFORMATION: Probe

<400> SEQUENCE: 7
cttcattgtt gcctttc                                                     17

<210> SEQ ID NO 8
<211> LENGTH: 15
<212> TYPE: DNA
<213> ORGANISM: Artificial Sequence
<220> FEATURE:
<223> OTHER INFORMATION: Probe

<400> SEQUENCE: 8
tcattgtggc ctttc                                                       15

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
tccacaggaa atccattgac                                                  20

<210> SEQ ID NO 10
```

```
<211> LENGTH: 27
<212> TYPE: DNA
<213> ORGANISM: Artificial Sequence
<220> FEATURE:
<223> OTHER INFORMATION: Primer

<400> SEQUENCE: 10
tctttagttc tcttagctaa ttcacca                                              27

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
cccagatgaa cgtcaacaac                                                      20

<210> SEQ ID NO 12
<211> LENGTH: 19
<212> TYPE: DNA
<213> ORGANISM: Artificial Sequence
<220> FEATURE:
<223> OTHER INFORMATION: Primer

<400> SEQUENCE: 12
gcacacgaat ccaatccag                                                       19

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13
gctcctaagc tcaacacaac c                                                    21

<210> SEQ ID NO 14
<211> LENGTH: 19
<212> TYPE: DNA
<213> ORGANISM: Artificial Sequence
<220> FEATURE:
<223> OTHER INFORMATION: Primer

<400> SEQUENCE: 14
ctggatgcaa tgggaagag                                                       19

<210> SEQ ID NO 15
<211> LENGTH: 22
<212> TYPE: DNA
<213> ORGANISM: Artificial Sequence
<220> FEATURE:
<223> OTHER INFORMATION: Primer

<400> SEQUENCE: 15
acgtcgtttc actctactcc tg                                                   22

<210> SEQ ID NO 16
<211> LENGTH: 21
<212> TYPE: DNA
<213> ORGANISM: Artificial Sequence
<220> FEATURE:
<223> OTHER INFORMATION: Primer

<400> SEQUENCE: 16
```

```
aggctgtcca cattctactc c                                              21

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
aactcgctaa ccgattcgac                                                20

<210> SEQ ID NO 18
<211> LENGTH: 22
<212> TYPE: DNA
<213> ORGANISM: Artificial Sequence
<220> FEATURE:
<223> OTHER INFORMATION: Primer

<400> SEQUENCE: 18
caatgccctt gatgataact cc                                             22

<210> SEQ ID NO 19
<211> LENGTH: 21
<212> TYPE: DNA
<213> ORGANISM: Artificial Sequence
<220> FEATURE:
<223> OTHER INFORMATION: Primer

<400> SEQUENCE: 19
gatcaattcc atctgcttcc a                                              21

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
ggtctccact ccacggttta                                                20

<210> SEQ ID NO 21
<211> LENGTH: 23
<212> TYPE: DNA
<213> ORGANISM: Artificial Sequence
<220> FEATURE:
<223> OTHER INFORMATION: Primer

<400> SEQUENCE: 21
gactggtttc tctgaagggt atg                                            23

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
ttgcttgcca atagcagttc                                                20

<210> SEQ ID NO 23
<211> LENGTH: 28
<212> TYPE: DNA
```

```
<213> ORGANISM: Artificial Sequence
<220> FEATURE:
<223> OTHER INFORMATION: Primer

<400> SEQUENCE: 23
gtttaaactt ccttcctaca gtgacagt                                           28

<210> SEQ ID NO 24
<211> LENGTH: 26
<212> TYPE: DNA
<213> ORGANISM: Artificial Sequence
<220> FEATURE:
<223> OTHER INFORMATION: Primer

<400> SEQUENCE: 24
catgtcgtag caggttacta atcaca                                             26

<210> SEQ ID NO 25
<211> LENGTH: 24
<212> TYPE: DNA
<213> ORGANISM: Artificial Sequence
<220> FEATURE:
<223> OTHER INFORMATION: Reporter sequence

<400> SEQUENCE: 25
ctgtagttat cttttaaatg atct                                               24

<210> SEQ ID NO 26
<211> LENGTH: 24
<212> TYPE: DNA
<213> ORGANISM: Artificial Sequence
<220> FEATURE:
<223> OTHER INFORMATION: Reporter sequence

<400> SEQUENCE: 26
ctgtagttat cttttaagtg atct                                               24

<210> SEQ ID NO 27
<211> LENGTH: 24
<212> TYPE: DNA
<213> ORGANISM: Artificial Sequence
<220> FEATURE:
<223> OTHER INFORMATION: Primer

<400> SEQUENCE: 27
ggcgactttg gtgaatacaa tcca                                               24

<210> SEQ ID NO 28
<211> LENGTH: 25
<212> TYPE: DNA
<213> ORGANISM: Artificial Sequence
<220> FEATURE:
<223> OTHER INFORMATION: Primer

<400> SEQUENCE: 28
caagctttgg catatgtcct ttagc                                              25

<210> SEQ ID NO 29
<211> LENGTH: 18
<212> TYPE: DNA
<213> ORGANISM: Artificial Sequence
<220> FEATURE:
<223> OTHER INFORMATION: Reporter sequence

<400> SEQUENCE: 29
ttgcattcct cagttgat                                                      18
```

<210> SEQ ID NO 30
<211> LENGTH: 18
<212> TYPE: DNA
<213> ORGANISM: Artificial Sequence
<220> FEATURE:
<223> OTHER INFORMATION: Reporter sequence

<400> SEQUENCE: 30
ttgcattcct ctgttgat                                                      18

<210> SEQ ID NO 31
<211> LENGTH: 29
<212> TYPE: DNA
<213> ORGANISM: Artificial Sequence
<220> FEATURE:
<223> OTHER INFORMATION: Primer

<400> SEQUENCE: 31
accttctatt ctgcaaggaa cttttttag                                          29

<210> SEQ ID NO 32
<211> LENGTH: 34
<212> TYPE: DNA
<213> ORGANISM: Artificial Sequence
<220> FEATURE:
<223> OTHER INFORMATION: Primer

<400> SEQUENCE: 32
tggacatcct tttctttata gattaaaact caat                                    34

<210> SEQ ID NO 33
<211> LENGTH: 22
<212> TYPE: DNA
<213> ORGANISM: Artificial Sequence
<220> FEATURE:
<223> OTHER INFORMATION: Reporter sequence

<400> SEQUENCE: 33 aaaaccttt taggtataga at                                                  22

<210> SEQ ID NO 34
<211> LENGTH: 18
<212> TYPE: DNA
<213> ORGANISM: Artificial Sequence
<220> FEATURE:
<223> OTHER INFORMATION: Reporter sequence

<400> SEQUENCE: 34
cctttttagg catagaat                                                      18

<210> SEQ ID NO 35
<211> LENGTH: 25
<212> TYPE: DNA
<213> ORGANISM: Artificial Sequence
<220> FEATURE:
<223> OTHER INFORMATION: Primer

<400> SEQUENCE: 35
ttgaattgca ccttgtggat ctttg                                              25

<210> SEQ ID NO 36
<211> LENGTH: 25
<212> TYPE: DNA
<213> ORGANISM: Artificial Sequence
<220> FEATURE:

<223> OTHER INFORMATION: Primer

<400> SEQUENCE: 36
ggacaaagag ttggagatga ggaaa                                          25

<210> SEQ ID NO 37
<211> LENGTH: 16
<212> TYPE: DNA
<213> ORGANISM: Artificial Sequence
<220> FEATURE:
<223> OTHER INFORMATION: Reporter sequence

<400> SEQUENCE: 37
tctccggaag acctag                                                    16

<210> SEQ ID NO 38
<211> LENGTH: 16
<212> TYPE: DNA
<213> ORGANISM: Artificial Sequence
<220> FEATURE:
<223> OTHER INFORMATION: Reporter sequence

<400> SEQUENCE: 38
tctccggagg acctag                                                    16

<210> SEQ ID NO 39
<211> LENGTH: 24
<212> TYPE: DNA
<213> ORGANISM: Artificial Sequence
<220> FEATURE:
<223> OTHER INFORMATION: Primer

<400> SEQUENCE: 39
ggtgatgatg ggagtctagc tttt                                           24

<210> SEQ ID NO 40
<211> LENGTH: 28
<212> TYPE: DNA
<213> ORGANISM: Artificial Sequence
<220> FEATURE:
<223> OTHER INFORMATION: Primer

<400> SEQUENCE: 40
gaatgtaatt ttctcaccag cactaacg                                       28

<210> SEQ ID NO 41
<211> LENGTH: 16
<212> TYPE: DNA
<213> ORGANISM: Artificial Sequence
<220> FEATURE:
<223> OTHER INFORMATION: Reporter sequence

<400> SEQUENCE: 41
attcctggaa acttca                                                    16

<210> SEQ ID NO 42
<211> LENGTH: 13
<212> TYPE: DNA
<213> ORGANISM: Artificial Sequence
<220> FEATURE:
<223> OTHER INFORMATION: Reporter sequence

<400> SEQUENCE: 42
cctgggaact tca                                                       13

<210> SEQ ID NO 43
<211> LENGTH: 24
<212> TYPE: DNA
<213> ORGANISM: Artificial Sequence
<220> FEATURE:
<223> OTHER INFORMATION: Primer

<400> SEQUENCE: 43
agttcttcac ctaagcttga ggat                                           24

<210> SEQ ID NO 44
<211> LENGTH: 23
<212> TYPE: DNA
<213> ORGANISM: Artificial Sequence
<220> FEATURE:
<223> OTHER INFORMATION: Primer

<400> SEQUENCE: 44
agcctcccta tcatgacttc cat                                            23

<210> SEQ ID NO 45
<211> LENGTH: 17
<212> TYPE: DNA
<213> ORGANISM: Artificial Sequence
<220> FEATURE:
<223> OTHER INFORMATION: Reporter sequence

<400> SEQUENCE: 45
acttgcacca cctaaaa                                                   17

<210> SEQ ID NO 46
<211> LENGTH: 16
<212> TYPE: DNA
<213> ORGANISM: Artificial Sequence
<220> FEATURE:
<223> OTHER INFORMATION: Reporter sequence

<400> SEQUENCE: 46 cttgcaccccc ctaaaa                                                   16

<210> SEQ ID NO 47
<211> LENGTH: 26
<212> TYPE: DNA
<213> ORGANISM: Artificial Sequence
<220> FEATURE:
<223> OTHER INFORMATION: Primer

<400> SEQUENCE: 47
tcccctaaac tgcagataga tgatga                                         26

<210> SEQ ID NO 48
<211> LENGTH: 19
<212> TYPE: DNA
<213> ORGANISM: Artificial Sequence
<220> FEATURE:
<223> OTHER INFORMATION: Primer

<400> SEQUENCE: 48
tcaatgcccc acagagcag                                                 19

<210> SEQ ID NO 49
<211> LENGTH: 18
<212> TYPE: DNA
<213> ORGANISM: Artificial Sequence
<220> FEATURE:
<223> OTHER INFORMATION: Reporter sequence

<400> SEQUENCE: 49
ttgcgctaac ctcctcct                                                     18

<210> SEQ ID NO 50
<211> LENGTH: 15
<212> TYPE: DNA
<213> ORGANISM: Artificial Sequence
<220> FEATURE:
<223> OTHER INFORMATION: Reporter sequence

<400> SEQUENCE: 50
cgctaaccgc ctcct                                                        15

<210> SEQ ID NO 51
<211> LENGTH: 20
<212> TYPE: DNA
<213> ORGANISM: Artificial Sequence
<220> FEATURE:
<223> OTHER INFORMATION: Primer

<400> SEQUENCE: 51
gaagggcaaa ccaggaaagg                                                   20

<210> SEQ ID NO 52
<211> LENGTH: 29
<212> TYPE: DNA
<213> ORGANISM: Artificial Sequence
<220> FEATURE:
<223> OTHER INFORMATION: Primer

<400> SEQUENCE: 52
caaaatacaa gcaaacaaat ttgtgttga                                         29

<210> SEQ ID NO 53
<211> LENGTH: 19
<212> TYPE: DNA
<213> ORGANISM: Artificial Sequence
<220> FEATURE:
<223> OTHER INFORMATION: Reporter sequence

<400> SEQUENCE: 53
caaggttagc taatatatg                                                    19

<210> SEQ ID NO 54
<211> LENGTH: 19
<212> TYPE: DNA
<213> ORGANISM: Artificial Sequence
<220> FEATURE:
<223> OTHER INFORMATION: Reporter sequence

<400> SEQUENCE: 54
caaggttagc tagtatatg                                                    19

<210> SEQ ID NO 55
<211> LENGTH: 106
<212> TYPE: DNA
<213> ORGANISM: Lycopersicon hirsutum
<220> FEATURE:
<221> NAME/KEY: misc_feature
<222> LOCATION: (75)..(75)
<223> OTHER INFORMATION: n is a, t, c, or g

<400> SEQUENCE: 55
gtcagtactc tccatttatt ttaatatttt agtttgtggg gttaaatatt tctcatgttt        60 ttgagggta tacanggtgt ttgtcatttt ctgtttattc aaatgt                      106

<210> SEQ ID NO 56
<211> LENGTH: 106
<212> TYPE: DNA
<213> ORGANISM: Lycopersicon esculentum
<220> FEATURE:
<221> NAME/KEY: misc_feature
<222> LOCATION: (75)..(75)
<223> OTHER INFORMATION: n is a, t, c, or g

<400> SEQUENCE: 56

```
gtcagtactc tccatttatt ttaatatttt agtttgtggg gttaactatt tctcatgttt    60
ttgaggggta tacanggtgt ttgtcattTt ctgtttattc aaatgt                  106
```

<210> SEQ ID NO 57
<211> LENGTH: 121
<212> TYPE: DNA
<213> ORGANISM: Lycopersicon hirsutum
<220> FEATURE:
<221> NAME/KEY: misc_feature
<222> LOCATION: (111)..(111)
<223> OTHER INFORMATION: n is a, t, c, or g

<400> SEQUENCE: 57

```
ttatgggata atagttgcaa gaaggaaggg caaaccagga aagggagaca aggttagcta    60
atatatgaat cttttaatca atcaacacaa atttgtttgc ttgtattttg ntatttgaca   120
c                                                                  121
```

<210> SEQ ID NO 58
<211> LENGTH: 121
<212> TYPE: DNA
<213> ORGANISM: Lycopersicon esculentum
<220> FEATURE:
<221> NAME/KEY: misc_feature
<222> LOCATION: (111)..(111)
<223> OTHER INFORMATION: n is a, t, c, or g

<400> SEQUENCE: 58

```
ttatgggata atagttgcaa gaaggaaggg caaaccagga aagggagaca aggttagcta    60
gtatatgaat cttttaatca atcaacacaa atttgtttgc ttgtattttg ntatttgaca   120
c                                                                  121
```

<210> SEQ ID NO 59
<211> LENGTH: 121
<212> TYPE: DNA
<213> ORGANISM: Lycopersicon hirsutum
<220> FEATURE:
<221> NAME/KEY: misc_feature
<222> LOCATION: (4)..(118)
<223> OTHER INFORMATION: n is a, t, c, or g

<400> SEQUENCE: 59

```
tgtnttTttt tttaaagcta tggtgcanag ttcttcacct aagcttgagg attttttagg    60
tggtgcaagt atggggaata gtcaatatgg aagtcatgat agggaggcta tggctttnag   120
c                                                                  121
```

<210> SEQ ID NO 60
<211> LENGTH: 121
<212> TYPE: DNA
<213> ORGANISM: Lycopersicon esculentum
<220> FEATURE:
<221> NAME/KEY: misc_feature
<222> LOCATION: (4)..(118)

```
<223> OTHER INFORMATION: n is a, t, c, or g

<400> SEQUENCE: 60 tgtnttttt tttaaagcta tggtgcanag ttcttcacct aagcttgagg attttttagg      60
gggtgcaagt atggggaata gtcaatatgg aagtcatgat agggaggcta tggctttnag    120
c                                                                    121

<210> SEQ ID NO 61
<211> LENGTH: 121
<212> TYPE: DNA
<213> ORGANISM: Lycopersicon hirsutum
<220> FEATURE:
<221> NAME/KEY: misc_feature
<222> LOCATION: (17)..(17)
<223> OTHER INFORMATION: n is a, t, c, or g

<400> SEQUENCE: 61
aatagctacc aggagtntat atgatgtcac taattactta gtattttctt gtcattcaat     60
atgaatacta gagagcctca atgttcacca acttgggtgt gtcatgacat atcatgctca   120
t                                                                    121

<210> SEQ ID NO 62
<211> LENGTH: 121
<212> TYPE: DNA
<213> ORGANISM: Lycopersicon esculentum
<220> FEATURE:
<221> NAME/KEY: misc_feature
<222> LOCATION: (17)..(17)
<223> OTHER INFORMATION: n is a, c, g, or t

<400> SEQUENCE: 62
aatagctacc aggagtntat atgatgtcac taattactta gtattttctt gtcattcaat     60
ttgaatacta gagagcctca atgttcacca acttgggtgt gtcatgacat atcatgctca   120
t                                                                    121

<210> SEQ ID NO 63
<211> LENGTH: 121
<212> TYPE: DNA
<213> ORGANISM: Lycopersicon hirsutum

<400> SEQUENCE: 63
aaaatagcca aataagacat gcctaatgat ctcggctggt ccttcactcc tggctttcaa     60
agtatgtgga tcagcacaaa gtttgagaat gaagcaatcc tcaccgttga tcttcttttc   120
t                                                                    121

<210> SEQ ID NO 64
<211> LENGTH: 121
<212> TYPE: DNA
<213> ORGANISM: Lycopersicon esculentum

<400> SEQUENCE: 64
aaaatagcca aataagacat gcctaatgat ctcggctggt ccttcactcc tggctttcaa     60
tgtatgtgga tcagcacaaa gtttgagaat gaagcaatcc tcaccgttga tcttcttttc   120
t                                                                    121
```

METHODS AND COMPOSITIONS FOR PRODUCING PLANTS WITH ELEVATED BRIX

CROSS-REFERENCE TO RELATED APPLICATIONS

This application claims the priority of U.S. Provisional Appl. Ser. No. 61/238,577, filed Aug. 31, 2009, the entire disclosure of which is incorporated herein by reference.

FIELD OF THE INVENTION

The present invention relates to the field of plant breeding and, more specifically, to methods and compositions for producing tomato plants with elevated Brix.

BACKGROUND OF THE INVENTION

The common tomato, *Lycopersicon esculentum* (Mill.), syn. *Solanum lycopersicum* is widely cultivated domestically and internationally. Of the approximately 500,000 acres of tomatoes grown annually in the United States, roughly 40% are grown for fresh market consumption, with the balance grown for processing.

One important goal of tomato breeding is to combine various desirable traits in a single variety/hybrid. Such desirable traits may include greater yield, resistance to diseases, insects or other pests, tolerance to heat and drought, better agronomic quality, higher nutritional value, enhanced growth rate and improved fruit properties. While breeding efforts to date have provided a number of useful tomato lines and varieties with beneficial traits, there remains a need in the art for new lines and varieties with further improved traits.

SUMMARY OF THE INVENTION

In one aspect, the invention provides a tomato plant comprising a hir4 allele of *Lycopersicon hirsutum* conferring elevated Brix, wherein the plant lacks an allele genetically linked to the hir4 allele of *Lycopersicon hirsutum* conferring poor plant habit. In a particular embodiment the tomato plant comprises the hir4 allele.

In another aspect, the invention provide a tomato plant or plant part of the invention. In particular embodiments, the plant part is a cell, a seed, a root, a stem, a leaf, a fruit, a flower, or pollen.

In a further aspect, the invention provides a method for obtaining a tomato plant comprising elevated Brix, comprising: a) obtaining a tomato plant heterozygous for a hir4 allele from *Lycopersicon hirsutum* that confers elevated Brix and is genetically linked in the plant to a *Lycopersicon hirsutum* allele that confers poor plant habit, wherein the plant is heterozygous relative to a corresponding locus in *Lycopersicon esculentum*; (b) obtaining progeny of the plant; and (c) selecting at least a first progeny plant in which genetic recombination has occurred such that the progeny comprises the hir4 allele but not the allele that confers poor plant habit. Plants produced by this method are also provided. For instance, a plant or part thereof produced by this method comprising a hir4 allele from *Lycopersicon hirsutum* that confers elevated Brix and lacks a *Lycopersicon hirsutum* allele genetically linked thereto that confers poor plant habit is provided by the invention.

In one embodiment, selecting a progeny plant comprises identifying a progeny plant that (1) comprises a genetic marker genetically linked to the hir4 allele in *Lycopersicon hirsutum* and/or lacks a genetic marker present at the corresponding locus from *Lycopersicon esculentum*, and (2) lacks a genetic marker genetically linked to the allele that confers poor plant habit in *Lycopersicon hirsutum* and/or comprises a genetic marker present at the corresponding locus from *Lycopersicon esculentum*. In another embodiment, selecting a progeny plant comprises detecting at least one allele selected from the group consisting of: a TG155 allele, a ANTL allele, a C2_At3g16150 allele, a cTOE-6-D11 allele, a CT50 allele, a C2_At4g33350 allele, a CT73 allele, a TG443 allele, a TG500 allele, an NL0233688 allele, an NL0233750 allele, an NL0233794 allele, an NL0233797 allele, an NL0233922 allele, an NL0234257 allele, an NL0234328 allele, an NL0234071 allele, an NL0234055 allele, an NL0233999 allele, and an NL0215788 allele.

In further embodiments, selected alleles are detected by a PCR-based method using oligonucleotide primer pair(s). For instance, the TG155 allele may be detected using the primer pair comprising SEQ ID NO:1 and SEQ ID NO:2; the ANTL allele may be detected using the primer pair comprising SEQ ID NO:9 and SEQ ID NO:10; the C2_At3g16150 allele may be detected using the primer pair comprising SEQ ID NO:11 and SEQ ID NO:12; the cTOE-6-D11 allele may be detected using the primer pair comprising SEQ ID NO:13 and SEQ ID NO:14; the CT50 allele may be detected using the primer pair comprising SEQ ID NO:15 and SEQ ID NO:16; the C2_At4g33350 allele may be detected using the primer pair comprising SEQ ID NO:17 and SEQ ID NO:18; the CT73 allele may be detected using the primer pair comprising SEQ ID NO:19 and SEQ ID NO:20; the TG443 allele may be detected using the primer pair comprising SEQ ID NO:21 and SEQ ID NO:22; the TG500 allele may be detected using the primer pair comprising SEQ ID NO:5 and SEQ ID NO:6; the NL0233688 allele may be detected using the primer pair comprising SEQ ID NO:23 and SEQ ID NO:24; the NL0233750 allele may be detected using the primer pair comprising SEQ ID NO:27 and SEQ ID NO:28; the NL0233794 allele may be detected using the primer pair comprising SEQ ID NO:31 and SEQ ID NO:32; the NL0233797 allele may be detected using the primer pair comprising SEQ ID NO:35 and SEQ ID NO:36; the NL0233922 allele may be detected using the primer pair comprising SEQ ID NO:39 and SEQ ID NO:40; the NL0234257 allele may be detected using the primer pair comprising SEQ ID NO:43 and SEQ ID NO:44; the NL0234328 allele may be detected using the primer pair comprising SEQ ID NO:47 and SEQ ID NO:48; or the NL0234071 allele may be detected using the primer pair comprising SEQ ID NO:51 and SEQ ID NO:52.

In other embodiments, selected alleles are detected by a PCR-based method using oligonucleotide primer pair(s) designed to detect the presence of a polymorphism defined between SEQ ID NOs:55-56; SEQ ID NOs:57-58; SEQ ID NOs:59-60; SEQ ID NOs:61-62; and/or SEQ ID NOs:63-64. In certain embodiments, detecting the allele comprises detecting a single nucleotide polymorphism at a position in the introgressed *L. hirsutum* sequence corresponding to nucleotide 46 of SEQ ID NO:55 or SEQ ID NO:56; nucleotide 61 of SEQ ID NO:57 or SEQ ID NO:58; nucleotide 61 of SEQ ID NO:59 or SEQ ID NO:60; nucleotide 61 of SEQ ID NO:61 or SEQ ID NO:62; or nucleotide 61 of SEQ ID NO:63 or SEQ ID NO:64.

In other embodiments, the NL0234055 allele may be detected using a primer pair designed to amplify a sequence within SEQ ID NO:55 and/or SEQ ID NO:56; the NL0234071 allele may be detected using a primer pair designed to amplify a sequence within SEQ ID NO:57 and/or SEQ ID NO:58; the NL0234257 allele may be detected using a primer pair designed to amplify a sequence within SEQ ID NO:59 and/or SEQ ID NO:60; the NL0233999 allele may be detected using a primer pair designed to amplify a sequence within SEQ ID NO:61 and/or SEQ ID NO:62; or the NL0215788 allele may be detected using a primer pair designed to amplify a sequence within SEQ ID NO:63 and/or SEQ ID NO:64.

In yet another aspect, the invention provides a method of producing a tomato plant comprising elevated Brix comprising introgressing into the plant a chromosomal segment comprising a hir4 allele of *Lycopersicon hirsutum* conferring elevated Brix, wherein the segment lacks a second allele genetically linked to the hir4 allele of *Lycopersicon hirsutum* conferring poor plant habit.

BRIEF DESCRIPTION OF THE DRAWINGS

FIG. 2A-D depicts Brix and plant habit data from the Chile field trial for recombinant classes: A) Brix and plant habit data comparison between class A and A'; B) Brix and plant habit data comparison between class A and the average of classes B', C', D', and E'; C) Brix and plant habit data comparison between the average for classes B, D, and E and the average of classes B', C', D', and E'; D) represents average values observed for Brix and plant habit for each class. Brix levels are reported as % soluble solids and plant habit is rated on a numerical scale where 1=acceptable plant habit and 9=poor plant habit. All error bars represent standard deviation.

FIG. 3A-G depicts Brix and plant habit data from the Chile field trial for individual plants. Two fixed genotypic classes of progeny were identified from each segregating heterozygous recombinant lineage, one fixed for *L. hirsutum* alleles in the introgression region ("hir"), and one fixed for *L. esculentum* alleles in the introgression (negative controls, designated "esc"). Brix levels are reported as % soluble solids and plant habit is rated on a numerical scale where 1=acceptable plant habit and 9=poor plant habit.

FIG. 4A-B depicts Brix and plant habit data from the Woodland, Calif. field trial for recombinant classes: A) Brix and plant habit data comparison between class A and A'; B) represents average values observed for Brix and plant habit for each class. Brix levels are reported as % soluble solids and plant habit is rated on a numerical scale where 1=acceptable plant habit and 9=poor plant habit. All error bars represent standard error.

FIG. 5A-K depicts Brix and plant habit data from the Woodland, Calif. field trial for individual plants. Two fixed genotypic classes of progeny were identified from each segregating heterozygous recombinant lineage, one fixed for *L. hirsutum* alleles in the introgression region ("hir"), and one fixed for *L. esculentum* alleles in the introgression (negative controls, designated "esc"). Brix levels are reported as % soluble solids and plant habit is rated on a numerical scale where 1=acceptable plant habit and 9=poor plant habit. All error bars represent standard error.

DETAILED DESCRIPTION OF THE INVENTION

Figure 1:
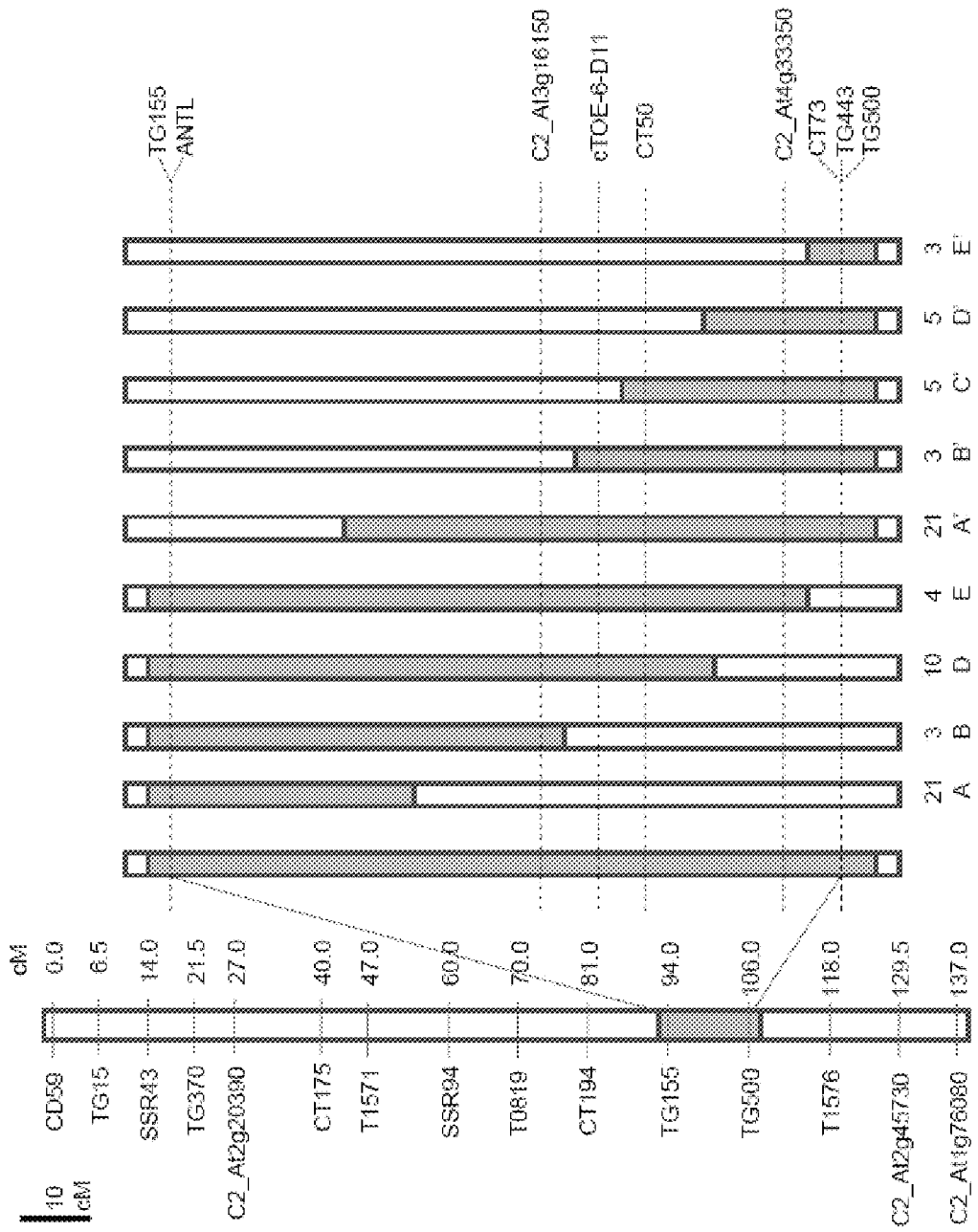
FIG. 1 depicts tomato chromosome 4, with DNA markers serving as reference points indicated on the left. Marker positions (in cM) from the publicly available Tomato-EXPENN2000 map (SOL Genomics Network, Cornell University) are indicated to the right of the chromosome. The call-out segments on the right depict the location of the TA517 hir4 introgression bred into PSQ-24-2189, delineated by markers TG155 and TG500, followed by hir4 recombinant classes recovered through fine-mapping efforts. White bars indicate *Lycopersicon esculentum* alleles and gray shaded bars indicate *Lycopersicon hirsutum* alleles. Recombination breakpoints are estimates based on marker genotype information. Different recombinant classes are indicated by letters, and the number of $F_3$ plants identified within each recombinant class is noted at the bottom of each segment.

The invention provides methods and compositions relating to plants, seeds and derivatives of tomato (*Lycopersicon esculentum*) plants comprising introgressions from *Lycopersicon hirsutum*, for instance, the hir4 allele(s), such that the plants comprising these recombinant introgressions display elevated levels of Brix without also displaying undesirable agronomic traits such as poor plant habit that have previously been transmitted with the elevated Brix trait. Lines containing the hir4 allele(s) are known and available, for example, from the Tomato Genetics Resource Center at University of California, Davis (http://tgrc.ucdavis.edu; Dept. of Plant Sciences, Mail Stop 3, University of California, One Shields Avenue, Davis, Calif. 95616, USA).

In certain embodiments, the invention relates to tomato plants comprising recombinant introgressions that retain hir4 alleles conferring elevated levels of Brix, but lack alleles derived from *Lycopersicon hirsutum* that are associated with poor plant habit. In certain embodiments, parts of plants of such lines are also contemplated, including cells, embryos, seeds, roots, stems, leaves, fruit, flowers, and pollen.

Another aspect of the current invention provides methods for obtaining a tomato plant comprising at least one recombinant *Lycopersicon hirsutum* introgression, wherein the tomato plant displays elevated levels of Brix but lacks poor plant habit. In certain embodiments, methods for obtaining such plants comprise obtaining a tomato plant heterozygous for the hir4 allele(s) from *Lycopersicon hirsutum*, obtaining progeny from such a plant, and selecting one or more such progeny plants wherein genetic recombination has surprisingly occurred such that the progeny comprises a hir4 allele but not an allele that confers poor plant habit.

In particular embodiments, the invention provides a method comprising obtaining a progeny plant that comprises such allele(s) by identifying one or more genetic markers genetically linked to the hir4 allele(s). Identifying the genetic markers may comprise a phenotypic, a genetic, or a biochemical test, and may include screening a parent and/or progeny plant for the presence of one or more of the alleles described herein, including, for example, one or more alleles of markers TG155, ANTL, NL0233688, NL0233750, NL0233794, NL0233797, NL0233922, NL0234257, NL0234328, and NL0234071 from *Lycopersicon hirsutum* and one or more alleles of marker C2_At3g16150 from *Lycopersicon esculentum*. The presence of alleles of other markers of interest including NL0234055, NL0233999, and NL0215788 may also be detected. In certain embodiments, one may screen for the presence of two or more genetic markers.

In certain embodiments, a method of the invention comprises identifying a tomato plant comprising a *Lycopersicon hirsutum*-derived introgression mapping between, and including one or more of, markers TG155 and TG500, wherein the introgression confers elevated levels of Brix, and lacks alleles conferring undesirable traits, such as poor plant habit. In particular embodiments, the method comprises identifying a tomato plant comprising a *Lycopersicon hirsutum* allele(s) at one or more of the following loci: TG155, ANTL, NL0233688, NL0233750, NL0233794, NL0233797, NL0233922, NL0234257, NL0234328, NL0234071, NL0234055, NL0233999, and NL0215788; and/or a *Lycopersicon esculentum* allele(s) at one or more of the following loci: C2_At3g16150 cTOE-6-D11, and CT50, that exhibits elevated levels of Brix and the absence of poor plant habit.

Quantitatively measurable traits that have been associated with improved tomato flavor include sugars and acids, collectively referred to as total soluble solids (TSS) or Brix (Fulton et al., 2002; Malundo et al., 1995). Brix levels in wild species of tomato have been reported to be as much as 15% of fruit fresh weight, which is approximately three times that of cultivated tomato varieties (Fridman et al., 2000). However, some QTLs associated with elevated Brix, such as those from *Lycopersicon hirsutum*, have thus far been associated with the undesirable trait of poor plant habit. The presence of these undesirable traits has hampered application of an elevation in Brix from this source in tomato plants. However, the present invention allows for the first time the decoupling of the elevated Brix and deleterious traits from *Lycopersicon hirsutum*. The invention therefore allows efficient screening for, and identification of, recombinant progeny tomato plants that comprise an introgressed region from *Lycopersicon hirsutum* conferring elevated Brix, while lacking *Lycopersicon hirsutum*-derived regions that contain QTLs for the undesirable trait.

Formation of a "recombinant" introgression is understood to be caused by recombination event(s) in close proximity to the hir4 QTL(s). Plants comprising a recombinant introgression, i.e. which have undergone a recombination event close to the QTL specifying elevated Brix, may efficiently be screened by use of molecular and/or phenotypic markers according to the methods provided herein. Thus, plant populations or progeny of such populations segregating (i.e. heterozygous) with respect to the QTLs specified by the hir4 introgressions may be screened for plants having a rare recombinant phenotype. Such plants can provide elevated Brix in combination with a lack of the poor plant habit trait associated with the herein described *Lycopersicon hirsutum* QTL(s).

A. Breeding of Tomato Lines Displaying Elevated Levels of Brix

One aspect of the current invention concerns methods for crossing a tomato line comprising a recombinant *Lycopersicon hirsutum* introgression conferring elevated levels of Brix with itself or a second plant and the seeds and plants produced by such methods. These methods can be used for production and propagation of cultivated tomato lines and hybrids displaying elevated levels of Brix without agronomically undesirable traits that have previously been associated with the elevated Brix traits.

In accordance with the invention, novel varieties may be created by crossing elevated Brix lines followed by generations of selection as desired and inbreeding for development of uniform lines. New varieties may also be created by crossing with any second plant. In selecting such a second plant to cross for the purpose of developing novel lines, it may be desired to choose those plants which either themselves exhibit one or more selected desirable characteristics or which exhibit the desired characteristic(s) when in hybrid combination. Once initial crosses have been made, inbreeding and selection are subsequently used to produce new varieties. For development of a uniform line, often five or more generations of selfing and selection are typically.

Uniform lines of new varieties may also be developed by way of doubled-haploids. This technique allows the creation of true breeding lines without the need for multiple generations of selfing and selection. In this manner true breeding lines can be produced in as little as one generation. Haploid embryos may be produced from microspores, pollen, anther cultures, or ovary cultures. The haploid embryos may then be doubled autonomously, or by chemical treatments (e.g. colchicine treatment). Alternatively, haploid embryos may be grown into haploid plants and treated to induce chromosome doubling. In either case, fertile homozygous plants are obtained. In accordance with the invention, any of such techniques may be used in connection with an elevated Brix line of the present invention and progeny thereof to achieve a homozygous line.

Backcrossing can also be used to improve an inbred plant. Backcrossing transfers a specific desirable trait, such as elevated levels of Brix, from one inbred or non-inbred source to an inbred that lacks that trait. This can be accomplished, for example, by first crossing a superior inbred (recurrent parent) to a donor source (nonrecurrent parent), which carries the appropriate locus or loci for the trait in question. The progeny of this cross are then mated back to the superior recurrent parent followed by selection in the resultant progeny for the desired trait to be transferred from the nonrecurrent parent. After five or more backcross generations with selection for the desired trait, the progeny are heterozygous for loci controlling the characteristic being transferred, but are like the superior parent for most or almost all other loci. The last backcross generation would be selfed to give pure breeding progeny for the trait being transferred. In this manner the recombined alleles provided by the invention may be introgressed into any tomato genotype.

Similarly, development of tomato varieties with improved traits by incorporation of alleles from a donor plant into an elite plant cultivar background can be accomplished efficiently using a method of Advanced Backcross QTL (AB-QTL) analysis (Tanksley and Nelson, 1996), followed by fine mapping analysis. Advanced backcross QTL analysis is a breeding strategy that allows the simultaneous identification of potentially useful alleles from donor germplasm and incorporation of those alleles into elite breeding material, using marker assisted selection. AB-QTL analysis is accomplished through the generation of a wild x elite hybrid, followed by a series of backcrosses to the elite parent, coupled with molecular marker and phenotypic selections. Backcross populations are subjected to QTL analysis for desirable traits, identifying genomic regions containing useful donor alleles that are introgressed into an elite cultivar genetic background, creating near isogenic lines (NILs). Finally, the NILs and the elite parent controls are evaluated for traits in replicated field trials (Bernacchi et al., 1998a). In addition to AB-QTL analysis, subsequent fine-mapping analysis is often used to pinpoint the alleles influencing the trait of interest and eliminate linkage to undesirable alleles. This is accomplished by additional backcrosses, generating subNILs with reduced overlapping introgressions, that are further characterized by QTL analysis and molecular markers to more precisely define the introgression segments contributing to desired traits.

The selection of a suitable recurrent parent is an important step for a successful backcrossing procedure. The goal of a backcross protocol is to alter or substitute a single trait or characteristic in the original variety. To accomplish this, a single locus of the recurrent variety is modified or substituted with the desired locus from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some commercially desirable trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Tomato varieties can also be developed from more than two parents. The technique, known as modified backcrossing, uses different recurrent parents during backcrossing. Modified backcrossing may be used to replace the original recurrent parent with a variety having certain more desirable characteristics or multiple parents may be used to obtain different desirable characteristics from each.

Many single locus traits have been identified that are not regularly selected for in the development of a new inbred but that can be improved by backcrossing techniques. Single locus traits may or may not be transgenic; examples of these traits include, but are not limited to, herbicide resistance, resistance to bacterial, fungal, or viral disease, insect resistance, modified fatty acid or carbohydrate metabolism, and altered nutritional quality. These comprise genes generally inherited through the nucleus.

Direct selection may be applied where the single locus acts as a dominant trait. Selection of tomato plants for breeding is not necessarily dependent on the phenotype of a plant and instead can be based on genetic investigations. For example, one can utilize a suitable genetic marker which is closely genetically linked to a trait of interest. One such marker can be used to identify the presence or absence of a trait in the offspring of a particular cross, and can be used in selection of progeny for continued breeding. This technique is commonly referred to as marker assisted selection. Any other type of genetic marker or other assay which is able to identify the relative presence or absence of a trait of interest in a plant can also be useful for breeding purposes.

General procedures for marker assisted selection are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

B. Plants Derived from a Tomato Line of the Present Invention by Genetic Engineering Many useful traits that can be introduced by backcrossing, as well as directly into a plant, are those which are introduced by genetic transformation techniques. Genetic transformation may therefore be used to insert a selected transgene into a plant of the invention or may, alternatively, be used for the preparation of transgenes which can be introduced by backcrossing. Methods for the transformation of plants that are well known to those of skill in the art and applicable to many crop species include, but are not limited to, electroporation, microprojectile bombardment, *Agrobacterium*-mediated transformation and direct DNA uptake by protoplasts.

Vectors used for the transformation of tomato cells are not limited so long as the vector can express an inserted DNA in the cells. For example, vectors comprising promoters for constitutive gene expression in tomato cells (e.g., cauliflower mosaic virus 35S promoter) and promoters inducible by exogenous stimuli can be used. Examples of suitable vectors include the pBI binary vector. The "tomato cell" into which the vector is to be introduced includes various forms of tomato cells, such as cultured cell suspensions, protoplasts, leaf sections, and callus.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

A particularly efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or NYTEX screen, onto a surface covered with target cells. The screen disperses the particles so that they are not delivered to the recipient cells in large aggregates. It is believed that a screen intervening between the projectile apparatus and the cells to be bombarded reduces the size of projectile aggregates and may contribute to a higher frequency of transformation by reducing the damage inflicted on the recipient cells by projectiles that are too large.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium* (and other *Rhizobia*), allowing for convenient manipulations (Klee et al., 1985; Broothaerts et al., 2005). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., 1985; U.S. Pat. No. 5,563,055).

Transformation of plant protoplasts also can be achieved using methods based on calcium phosphate precipitation, polyethylene glycol treatment, electroporation, and combinations of these treatments (see, e.g., Potrykus et al., 1985;

Omirulleh et al., 1993; Fromm et al., 1986; Uchimiya et al., 1986; Marcotte et al., 1988). Transformation of plants and expression of foreign genetic elements is exemplified in Choi et al. (1994) and Ellul et al. (2003).

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for tomato plant gene expression include, but are not limited to, the cauliflower mosaic virus (CaMV) P-35S promoter, which confers constitutive, high-level expression in most plant tissues (see, e.g., Odel et al., 1985), including monocots (see, e.g., Dekeyser et al., 1990; Terada and Shimamoto, 1990); a tandemly duplicated version of the CaMV 35S promoter, the enhanced 35S promoter (P-e35S), the nopaline synthase promoter (An et al., 1988), the octopine synthase promoter (Fromm et al., 1989); and the figwort mosaic virus (P-FMV) promoter as described in U.S. Pat. No. 5,378,619 and an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, and other plant DNA virus promoters known to express in plant cells.

A variety of plant gene promoters that are regulated in response to environmental, hormonal, chemical, and/or developmental signals can be used for expression of an operably linked gene in plant cells, including promoters regulated by (1) heat (Callis et al., 1988), (2) light (e.g., pea rbcS-3A promoter, Kuhlemeier et al., 1989; maize rbcS promoter, Schaffner and Sheen, 1991; or chlorophyll a/b-binding protein promoter, Simpson et al., 1985), (3) hormones, such as abscisic acid (Marcotte et al., 1989), (4) wounding (e.g., wun1, Siebertz et al., 1989); or (5) chemicals such as methyl jasmonate, salicylic acid, or Safener. It may also be advantageous to employ organ-specific promoters (e.g., Roshal et al., 1987; Schernthaner et al., 1988; Bustos et al., 1989).

Exemplary nucleic acids which may be introduced to the tomato plants of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a tomato plant according to the invention. Non-limiting examples of particular genes and corresponding phenotypes one may choose to introduce into a tomato plant include one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference in their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., 1991). The RNA could also be a catalytic RNA molecule (i.e., a ribozyme) engineered to cleave a desired endogenous mRNA product (see for example, Gibson and Shillito, 1997). Thus, any gene which produces a protein or mRNA which expresses a phenotype or morphology change of interest is useful for the practice of the present invention.

C. Definitions

In the description and tables herein, a number of terms are used. In order to provide a clear and consistent understanding of the specification and claims, the following definitions are provided:

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Brix: The content of total soluble solids, such as sugars and acids, in a tomato.

Cultivated tomato: Tomato which is suitable for consumption and meets the requirements for commercial cultivation, e.g. typically classified as *Lycopersicon esculentum*. In addition to the tomato plants themselves, and the parts thereof suitable for consumption, such as the fruit, the invention comprises parts or derivatives of the plant suitable for propagation. Examples of parts suitable for propagation are organ tissues, such as leaves, stems, roots, shoots and the like, protoplasts, somatic embryos, anthers, petioles, cells in culture and the like. Derivatives suitable for propagation are for instance seeds. The plants according to the invention can be cultivated or propagated in the conventional manner but also by means of tissue culture techniques from plant parts.

Crossing: The mating of two parent plants.

Cross-pollination: Fertilization by the union of two gametes from different plants.

Diploid: A cell or organism having two sets of chromosomes.

Emasculate: The removal of plant male sex organs or the inactivation of the organs with a cytoplasmic or nuclear genetic factor or a chemical agent conferring male sterility.

Enzymes: Molecules which can act as catalysts in biological reactions.

$F_1$ Hybrid: The first generation progeny of the cross of two nonisogenic plants.

Genotype: The genetic constitution of a cell or organism.

Haploid: A cell or organism having one set of the two sets of chromosomes in a diploid.

Linkage: A phenomenon wherein alleles on the same chromosome tend to segregate together more often than expected by chance if their transmission was independent.

LOD score: The level of confidence in an estimate of linkage distance between two loci.

Marker: A readily detectable phenotype or genotype, preferably inherited in codominant fashion (both alleles at a locus in a diploid heterozygote are readily detectable), with no environmental variance component, i.e., heritability of 1.

Phenotype: The detectable characteristics of a cell or organism, which characteristics are the manifestation of gene expression.

Poor Plant Habit: Poor plant habit is characterized by increased plant vegetative growth. A tomato plant with poor plant habit exhibits increased vegetative growth in comparison with a cultivated tomato plant of desirable plant habit with more defined vegetative growth. Tomato plant habit is rated on a scale of 1 to 9, where 1 is acceptable plant habit and 9 is poor plant habit.

Quantitative Trait Loci (QTL): Quantitative trait loci (QTL) refer to genetic loci that control to some degree numerically representable traits that are usually continuously distributed.

Recombination event is understood to mean a meiotic crossing-over.

Regeneration: The development of a plant from tissue culture.

Self-pollination: The transfer of pollen from the anther to the stigma of the same plant.

Single Locus Converted (Conversion) Plant: Plants which are developed by a plant breeding technique called backcrossing, wherein essentially all of the morphological and physiological characteristics of a tomato variety are recovered in addition to the characteristics of the single locus transferred into the variety via the backcrossing technique and/or by genetic transformation.

Substantially Equivalent: A characteristic that, when compared, does not show a statistically significant difference (e.g., p=0.05) from the mean.

Tissue Culture: A composition comprising isolated cells of the same or a different type or a collection of such cells organized into parts of a plant.

Transgene: A genetic locus comprising a sequence which has been introduced into the genome of a tomato plant by transformation.

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

EXAMPLES

Example 1

Creation of *L. esculentum* Plants with *L. hirsutum* Introgression and Verification Thereof Elite breeding lines with (TA517) and without (99GHB1136.1005) a *Lycopersicon hirsutum* introgression on the long arm of chromosome 4 conferring elevated Brix were crossed to produce $F_1$ progeny. TA517, a high Brix line with an *L. hirsutum* introgression, was obtained from Dr. Steven Tanksley at Cornell University (Bernacchi et al., *Theor. Appl. Genet.*, 97:170-180, 1998b; Monforte and Tanksley, *Genome*, 43:803, 2000). 99GHB1136.1005 is a proprietary inbred line.

Proprietary line 99GHB1136.1005 was crossed to TA517, followed by four backcrosses to inbred line HP987, followed by six generations of pedigree selection and then bulking in BC4F6. This combination of crossing, backcrossing and pedigree selection yielded tomato line PSQ-24-2189. All crossing and pedigree selection was done in field plots and greenhouses in Woodland, Calif. and Colina and Melipilla, Chile. These crosses were made as indicated below.

| Year 1 Woodland | F1 | 99GHB1136.1005 × TA517 |
|---|---|---|
| | ↓ | |
| Year 1 Woodland | BC1 | ([(99GHB1136.1005) TA517 × HP 987 |
| | ↓ | |
| Year 2 Woodland | BC2 | ([(99GHB1136.1005) TA517]HP987 × HP987 |
| | ↓ | |
| Year 3 Woodland | BC2F2 | |
| | ↓ | |
| Year 3 Woodland | BC2F3 | |
| | ↓ | |
| Year 4 Woodland | BC3 | ([(99GHB1136.1005) TA517] HP987)HP987 × HP987 |
| | ↓ | |
| Year 5 Woodland | BC3F2 | |
| | ↓ | |
| Year 5 Woodland | BC4 | [([(99GHB1136.1005) TA517] HP987)HP987]HP987 × HP987 |
| | ↓ | |
| Year 5 Woodland | BC4F2 | |
| | ↓ | |
| Year 6 Woodland | BC4F3 | |
| | ↓ | |
| Year 6 Woodland | BC4F4 | |
| | ↓ | |
| Year 7 Chile | BC4F5 | |
| | ↓ | |
| Year 7 Woodland | BC4F6 | Line designated PSQ-24-2189 |

PSQ-24-2189 (the elevated Brix level donor line) was then crossed to PSQ-25-252 (the recipient line). The $F_1$ created from this cross was selfed to produce $F_2$ progeny in the field. These $F_2$ progeny were screened using markers (TG155 and TG500) flanking the introgression site in order to identify progeny heterozygous for the introgressed region from *Lycopersicon hirsutum*. Heterozygous $F_2$ plants were selfed to produce segregating $F_3$ progeny, which were screened with markers TG155 and TG500 to identify rare recombinants within the introgressed region. These crosses were made as indicated below.

| | PSQ-24-2189 (donor) × PSQ-25-252 (recipient) | | | |
|---|---|---|---|---|
| Sp Year 8 | $F_1$ | | | |
| | ↓ | | | |
| Su Year 8 | $F_2$ | | | |
| | ↓ | | | |
| W Year 9 | ++ | +/− | | −− |
| | ↓ | | | |

-continued

| | | PSQ-24-2189 (donor) × PSQ-25-252 (recipient) |
|---|---|---|
| Sp/Su Year 9 | F₃ ↓ | Large F₃ population derived from heterozygous F₂ plants; 3072 F₃ plants screened with flanking markers to identify recombinants. |
| W Year 10 | F₄ | 45 recombinants were selfed; 45 F₃ families were identified with markers then transplanted in a Randomized Complete Block Design (RCBD) for field trial in Chile: phenotyped for Brix and plant habit. |
| Su Year 10 | F₄ | 74 F₃ recombinants were selfed; screened with flanking markers to identify fixed genotypic classes then transplanted in RCBD for field trial in Woodland: phenotyped for Brix and plant habit. |

Markers TG155 and TG500 are available as Taqman assays. See Table 1 for details.

TABLE 1

Taqman assay details for TG155 and TG500.

| Marker | Trait Allele 1 | Trait Allele 2 | Dye 1 | Allele 2 | Allele 2 | Dye 2 | Fwd Primer | SEQ ID NO: | Rev Primer | SEQ ID NO: | Rev Primer | SEQ ID NO: | Rev Primer | SEQ ID NO: |
|---|---|---|---|---|---|---|---|---|---|---|---|---|---|---|
| TG155 | T | hir | VIC | C | esc | FAM | TGAACTTG AATCTCCT CTTCATTT TGATGA | 1 | AGTTCTTC ACCTAAGC TTGAGGAT TTT | 2 | CTATGGCT TTaAGCTT AG | 3 | ATGGCTTT gAGCTTAG | 4 |
| TG500 | C | hir | FAM | A | esc | VIC | TCATCCAA ACTCTGCT GAACATCA | 5 | ATGTTGAT CTCTTTGC AGTAGGCA | 6 | CTTCATTG TtGCCTTT C | 7 | TCATTGTg GCCTTTC | 8 |

The Taqman protocol was as follows. Reaction volumes of 5 μL are comprised of the following components: 0.4375 μL water, 2.5 μL 2× mix with ROX, 0.0625 μL 80× mix, and 2 μL template. Thermocycler conditions were as follows: initial hold of 50 C for 2 minutes, followed by a hold of 95 C for 2 minutes, followed by 40 cycles of: 95 C for 15 seconds, 60 C for 1 minute; with a final hold at 25 C. Following thermal cycling, reactions were analyzed on an ABI 7900 plate reader.

FIG. 1 shows the approximate location of the introgression from *Lycopersicon hirsutum* and the relative positions of markers TG155 and TG500. Table 2 shows the results of the screen. Seventy-five F₃ recombinants were identified and confirmed from 3072 plants screened.

TABLE 2

Results of screening with flanking markers TG155 and TG500 in the F₃ population to identify hir4 introgression recombinants.

| Species Introgression | Flanking Markers | Progeny Screened | Verified Recombinants |
|---|---|---|---|
| *L. hirsutum* | TG155 and TG500 | 3072 | 75 |

Example 2

Genotyping of the F₃ Population

Field analysis through development of the pedigree represented in Example 1 indicated linkage between the *L. hirsutum* introgression fragment (yielding increased Brix levels) and poor plant habit. To identify and provide the ability to track a linkage breaking event between the high Brix QTL and the QTL contributing to poor plant habit, additional markers interstitial to markers TG155 and TG500 were developed. Cleaved amplified polymorphic sequence (CAPS) assays for each of the interstitial markers shown in Table 3 were developed by performing sequence analysis, designing primers for PCR amplification, confirming adequate amplification, and screening for polymorphisms.

TABLE 3

Marker sequence and assay information.

| | Forward Primer | SEQ ID NO: | Reverse Primer | SEQ ID NO: | Profile | CAPS |
|---|---|---|---|---|---|---|
| ANTL | TCCACAGGAAATCCATT GAC | 9 | TCTTTAGTTCTCTTAGCTA ATTCACCA | 10 | 51long | HaeIII |
| C2_At3g161 50 | CCCAGATGAACGTCAAC AAC | 11 | GCACACGAATCCAATCCAG | 12 | TD58-52long | HincII |
| cTOE-6-D11 | GCTCCTAAGCTCAACAC AACC | 13 | CTGGATGCAATGGGAAGAG | 14 | TD58-52long | HhaI, or BsaAI |
| CT50 | ACGTCGTTTCACTCTAC TCCTG | 15 | AGGCTGTCCACATTCTACT CC | 16 | TD62-56long | NgoMIV |
| C2_At4g333 50 | AACTCGCTAACCGATTC GAC | 17 | CAATGCCCTTGATGATAAC TCC | 18 | TD58-52long | BsaAI |
| CT73 | GATCAATTCCATCTGCT TCCA | 19 | GGTCTCCACTCCACGGTTT A | 20 | TD58-52long | MnlI |

TABLE 3-continued

Marker sequence and assay information.

| | Forward Primer | SEQ ID NO: | Reverse Primer | SEQ ID NO: | Profile | CAPS |
|---|---|---|---|---|---|---|
| TG443 | GACTGGTTTCTCTGAAGGGTATG | 21 | TTGCTTGCCAATAGCAGTTC | 22 | TD58-52long | AseI |

To set up the PCR portion of the marker CAPS assays, 7 µL reactions were prepared according to the following protocol: 3.5 µL USB 2× mix, 0.47 µL forward primer (5 µM), 0.47 µL reverse primer (5 µM), 2 µL template, 0.56 µL water. Thermal cycling profiles were specified as follows.

TD62-56 long PCR profile: Initial hold of 95 C for 5 minutes; 12 cycles of the following: 95 C for 30 seconds, 62 C* for 30 seconds, 72 C for 3 minute and 30 seconds where "*" indicates a −0.5 C decrease per cycle in annealing temperature from 62 C to a final annealing temperature of 56 C. This was followed by 23 cycles of the following: 95 C for 30 seconds, 56 C for 30 seconds, 72 C for 3 minute and 30 seconds with a final extension of 72 C for 7 minutes and a final hold at 25 C.

TD58-52 long PCR profile: Initial hold of 95 C for 5 minutes; 12 cycles of the following: 95 C for 30 seconds, 58 C* for 30 seconds, 72 C for 3 minute and 30 seconds where "*" indicates a −0.5 C decrease per cycle in annealing temperature from 58 C to a final annealing temperature of 52 C. This was followed by 23 cycles of the following: 95 C for 30 seconds, 52 C for 30 seconds, 72 C for 3 minute and 30 seconds with a final extension of 72 C for 7 minutes and a final hold at 25 C.

51 long PCR profile: Initial hold of 95 C for 5 minutes; 35 cycles of the following: 95 C for 30 seconds, 50 C for 30 seconds, 72 C for 3 minute and 30 seconds with a final extension of 72 C for 7 minutes and a final hold at 25 C.

Following PCR amplification, reaction products were digested with the appropriate restriction enzyme mix. The enzyme mix was prepared according to the following specifications: 3 µL total reaction volume consisting of 0.93 µL 10×BSA, 1.8 µL 10× buffer, and 0.27 µL enzyme.

To perform the CAPS assay, 3 µL of restriction enzyme mix was added to each PCR reaction and the digestion reactions were incubated at the appropriate temperature for the enzyme for at least three hours. Following digestion of the PCR product, the reactions were run out on a 2% agarose gel for approximately 1.5-2 hours at 120 volts in 1×TAE buffer.

Of the 75 confirmed $F_3$ recombinants from Example 1, forty-two had recombination breakpoints between markers ANTL and C2_At3g16150 (1.37% recombination frequency; recombinant classes A and A' in FIG. 1); six plants (0.20%) had breakpoints between markers C2_At3g16150 and cTOE-6-D11 (recombinant classes B and B' in FIG. 1); five (0.16%) had breakpoints between markers cTOE-6-D11 and CT50 (recombinant class C', FIG. 1); fifteen (0.49%) had breakpoints between markers CT50 and C2_At4g33350 (recombinant classes D and D', FIG. 1) and seven plants (0.23%) had recombination breakpoints between markers C2_At4g33350 and CT73 (recombinant classes E and E', FIG. 1). No plants were identified for recombinant class C, i.e. with *L. hirsutum* alleles at TG155 and a breakpoint between markers cTOE-6-D11 and CT50. Recombinant $F_3$ progeny were next selfed to fix the recombinant genotypes. Selfed progeny were screened once more with flanking markers to recover and verify homozygous plants fixed for the recombinant genotypes. Phenotyping of the homozygous recombinants allowed a more precise determination of the position of the Brix locus.

Example 3

Field Trials Demonstrating Retention of Elevated Brix and Elimination of Undesirable Traits in Plants Grown in Chile 45 of the 75 segregating recombinant $F_4$ families were grown in Chile in year 10, and evaluated for Brix and plant habit. Fine mapping evaluation of these lines with the marker panel represented in Table 2 was undertaken to determine recombinant lines in which linkage was broken between the desired elevated levels of Brix and the undesired poor plant habit traits from *Lycopersicon hirsutum*. Depending on the presence of either the *Lycopersicon hirsutum* (hir) or *Lycopersicon esculentum* (esc) allele at each marker position monitored, recombinants were bulked into classes. Table 4 details the classes, which are also represented schematically in FIG. 1 and were introduced in Example 2. No recombinants were recovered for class C.

TABLE 4

Recombinant class designation by marker genotype.

| Class | TG155/ANTL | C2_At3g16150 | cTOE-6-D11 | CT50 | C2_At4g33350 | CT73/TG443/TG500 |
|---|---|---|---|---|---|---|
| A | hir | esc | esc | esc | esc | esc |
| B | hir | hir | esc | esc | esc | esc |
| D | hir | hir | hir | hir | esc | esc |
| E | hir | hir | hir | hir | hir | esc |
| A' | esc | hir | hir | hir | hir | hir |
| B' | esc | esc | hir | hir | hir | hir |
| C' | esc | esc | esc | hir | hir | hir |
| D' | esc | esc | esc | esc | hir | hir |
| E' | esc | esc | esc | esc | esc | hir |

Marker genotypes at the interstitial markers were correlated to plant phenotype to provide means for identifying recombinants of interest. The data represented in FIG. 2 indicates a correlation between elevated Brix with an associated increase in poor plant habit and the chromosomal segment introgressed from *Lycopersicon hirsutum* in the region between markers TG155/ANTL and C2_At3g16150.

Utilizing this information, work was then focused on individual plants within the Class A designation in efforts to identify and molecularly characterize a recombinant demonstrating increased levels of Brix and acceptable plant habit (FIG. 4). Among the recombinant classes with *L. hirsutum* alleles between markers TG155/ANTL and C2_At3g16150, Class A collectively contains the smallest introgressed region from *L. hirsutum* with a corresponding increase in Brix levels. FIG. 3 details Brix and plant habit phenotypes for individual Class A recombinants from this trial.

Example 4

Field Trials Demonstrating Retention of Elevated Brix and Elimination of Undesirable Traits in Plants Grown in Woodland, Calif.

Field evaluations were repeated in Woodland, Calif. in year 10. Fixed progeny for twenty-seven of the original 75 recombinants were evaluated in this trial. As in the Chile trial in Example 3, *L. esculentum* controls (esc) were identified from the same segregating lineage, to minimize background effects.

Evaluation of the previously generated genotypic and phenotypic data available for the lines along with the phenotypic data obtained from the Woodland, Calif. field trial was undertaken to confirm results from Chile and to identify recombinant lines in which linkage was broken between the desired elevated Brix and the undesired poor plant habit traits from *L. hirsutum*. Recombinant plants were again bulked into classes depending on the presence of either the *L. hirsutum* (hir) or *L. esculentum* (esc) allele at each marker position monitored. Results from the Woodland, Calif. field trial are shown in FIG. 4. These results, taken into account with the results from Chile, indicate the recombinant fragments bulked into Class A show increased Brix with a potential for acceptable plant habit. Data from evaluation of individual recombinant plants from the Woodland, Calif. field trial within the Class A group is represented in FIG. 5.

Example 5

Identification of Lines Demonstrating Elevated Brix and Acceptable Plant Habit

Analysis of marker genotype with plant phenotype, from the Chile and California field trials (Examples 3 and 4), led to the identification of seven recombinants with linkage broken between elevated Brix and poor plant habit. See FIGS. 3 and 5, recombinants A_01, A_02, A_03, A_05, A_06, A_07, and A_09. Of these seven, three recombinants, A_01, A_06, and A_09, exhibit the most desirable linkage-breaking elevated Brix and acceptable plant habit profiles.

Example 6

Fine Mapping Linkage Breaking Events

To further delineate recombination breakpoints resulting in this linkage breaking event, further fine mapping will be undertaken. SNP markers converted to Taqman assays were tested on *L. esculentum* and *L. hirsutum*, line LA1777, controls to determine if polymorphic distinction exists in those ten markers. Of those tested, eight were polymorphic between the two controls. These eight markers, noted in Table 5 below, were used to further map the linkage breaking recombination break point in the seven lines listed in Example 5 above, and used as tracking markers for identification of those recombination events (also see Example 7).

TABLE 5

SNP marker Taqman assays for linkage breaking fine mapping and identification of recombinant events.

| Assay | Forward Primer | SEQ ID NO: | Reverse Primer | SEQ ID NO: | Reporter Dye 1 | Allele 1 | Reporter Sequence 1 | SEQ ID NO: | Reporter Dye 2 | Allele 2 | Reporter Sequence 2 | SEQ ID NO: |
|---|---|---|---|---|---|---|---|---|---|---|---|---|
| NL0233688 | GTTTAAACTTCCTTCCTACAGTGACAGT | 23 | CATGTCGTAGCAGGTTACTAATCACA | 24 | VIC | esc | CTGTAGTTATCTTTTAAATGATCT | 25 | FAM | hir | CTGTAGTTATCTTTTAAGTGATCT | 26 |
| NL0233750 | GGCGACTTTGGTGAATACAATCCA | 27 | CAAGCTTTGGCATATGTCCTTTAGC | 28 | VIC | esc | TTGCATTCCTCAGTTGAT | 29 | FAM | hir | TTGCATTCCTCTGTTGAT | 30 |
| NL0233794 | ACCTTCTATTCTGCAAGGAACTTTTTTAG | 31 | TGGACATCCTTTTCTTTATAGATTAAAACTCAAT | 32 | VIC | esc | AAAACCTTTTTAGGTATAGAAT | 33 | FAM | hir | CCTTTTTAGGCATAGAAT | 34 |
| NL0233797 | TTGAATTGCACCTTGTGGATCTTTG | 35 | GGACAAAGAGTTGGAGATGAGGAAA | 36 | VIC | esc | TCTCCGGAAGACCTAG | 37 | FAM | hir | TCTCCGGAGGACCTAG | 38 |
| NL0233922 | GGTGATGATGGGAGTCTAGCTTTT | 39 | GAATGTAATTTTCTCACCAGCACTAACG | 40 | VIC | hir | ATTCCTGGAAACTTCA | 41 | FAM | esc | CCTGGGAACTTCA | 42 |
| NL0234257 | AGTTCTTCACCTAAGCTTGAGGAT | 43 | AGCCTCCCTATCATGACTTCCAT | 44 | VIC | hir | ACTTGCACCACCTAAAA | 45 | FAM | esc | CTTGCACCCCCTAAAA | 46 |

TABLE 5-continued

SNP marker Taqman assays for linkage breaking fine mapping and identification of recombinant events.

| Assay | Forward Primer | SEQ ID NO: | Reverse Primer | SEQ ID NO: | Reporter Dye 1 | Allele 1 | Reporter Sequence 1 | SEQ ID NO: | Reporter Dye 2 | Allele 2 | Reporter Sequence 2 | SEQ ID NO: |
|---|---|---|---|---|---|---|---|---|---|---|---|---|
| NL0234328 | TCCCCTAAA CTGCAGATA GATGATGA | 47 | TCAATGCCC CACAGAGCA G | 48 | VIC | hir | TTGCGCTAAC CTCCTCCT | 49 | FAM | esc | CGCTAACCGCC TCCT | 50 |
| NL0234071 | GAAGGGCAA ACCAGGAAA GG | 51 | CAAAATACA AGCAAACAA ATTTGTGTT GA | 52 | VIC | hir | CAAGGTTAGC TAATATATG | 53 | FAM | esc | CAAGGTTAGCT AGTATATG | 54 |

Example 7

Identification of Additional Markers and Further Fine Mapping in hir4 Brix QTL Region Additional genetic mapping in the hir4 region of chromosome 4 was performed, allowing for creation of a revised genetic map for improved discrimination of the Brix QTL position and localization of recombinant breakpoints. The QTL location was defined between markers NL0234055 and NL0215788 of the revised genetic map. For comparison with the map shown in FIG. 1, markers TG155 and CT50 are now found at positions 82.2 cM and 87.0 cM, respectively, on the revised genetic map, while new or revised map positions for each of markers NL0234055, NL0234071, NL0234257, NL0233999, and NL0215788 are given in Table 6, at positions between 85.2 cM and 89 cM. The sequences (SEQ ID NOs. 55-64) given in Table 6 define single nucleotide polymorphisms which may be utilized to create PCR-based assays to identify recombinant lines of interest containing the desired Brix phenotype, no exhibition of poor plant habit, and a smaller *L. hirsutum* introgression fragment. For instance, marker NL0234055 is defined by a SNP at position 46 of SEQ ID NOs: 55-56.

TABLE 6

Additional genetic markers and SNP's for designing PCR assays to define linkage break points for fine mapping and identification of recombinant events on chromosome 4. "Allele 1" represents *L. hirsutum*-derived sequence, while "Allele 2" represents *L. esculentum*-derived sequence.

| Marker (allele #) | Map position (cM) | Sequence for assay design | SEQ ID NO: |
|---|---|---|---|
| NL0234055 (allele 1) | 85.2 | GTCAGTACTCTCCATTTATTTTAAT ATTTTAGTTTGTGGGGTTAAATATT TCTCATGTTTTTGAGGGGTATACAN GGTGTTTGTCATTTTCTGTTTATTC AAATGT | 55 |
| NL0234055 (allele 2) | 85.2 | GTCAGTACTCTCCATTTATTTTAAT ATTTTAGTTTGTGGGGTTAACTATT TCTCATGTTTTTGAGGGGTATACAN GGTGTTTGTCATTTTCTGTTTATTC AAATGT | 56 |
| NL0234071 (allele 1) | 85.2 | TTATGGGATAATAGTTGCAAGAAGG AAGGGCAAACCAGGAAAGGGAGACA AGGTTAGCTAATATATGAATCTTTT AATCAATCAACACAAATTTGTTTGC TTGTATTTTGNTATTTGACAC | 57 |
| NL0234071 (allele 2) | 85.2 | TTATGGGATAATAGTTGCAAGAAGG AAGGGCAAACCAGGAAAGGGAGACA AGGTTAGCTAGTATATGAATCTTTT AATCAATCAACACAAATTTGTTTGC TTGTATTTTGNTATTTGACAC | 58 |
| NL0234257 (allele 1) | 85.2 | TGTNTTTTTTTTTAAAGCTATGGTG CANAGTTCTTCACCTAAGCTTGAGG ATTTTTTAGGTGGTGCAAGTATGGG GAATAGTCAATATGGAAGTCATGAT AGGGAGGCTATGGCTTTNAGC | 59 |
| NL0234257 (allele 2) | 85.2 | TGTNTTTTTTTTTAAAGCTATGGTG CANAGTTCTTCACCTAAGCTTGAGG ATTTTTTAGGGGGTGCAAGTATGGG GAATAGTCAATATGGAAGTCATGAT AGGGAGGCTATGGCTTTNAGC | 60 |
| NL0233999 (allele 1) | 88.7 | AATAGCTACCAGGAGTNTATATGAT GTCACTAATTACTTAGTATTTTCTT GTCATTCAATATGAATACTAGAGAG CCTCAATGTTCACCAACTTGGGTGT GTCATGACATATCATGCTCAT | 61 |
| NL0233999 (allele 2) | 88.7 | AATAGCTACCAGGAGTNTATATGAT GTCACTAATTACTTAGTATTTTCTT GTCATTCAATTTGAATACTAGAGAG CCTCAATGTTCACCAACTTGGGTGT GTCATGACATATCATGCTCAT | 62 |
| NL0215788 (allele 1) | 89 | AAAATAGCCAAATAAGACATGCCTA ATGATCTCGGCTGGTCCTTCACTCC TGGCTTTCAAAGTATGTGGATCAGC ACAAAGTTTGAGAATGAAGCAATCC TCACCGTTGATCTTCTTTTCT | 63 |
| NL0215788 (allele 2) | 89 | AAAATAGCCAAATAAGACATGCCTA ATGATCTCGGCTGGTCCTTCACTCC TGGCTTTCAATGTATGTGGATCAGC ACAAAGTTTGAGAATGAAGCAATCC TCACCGTTGATCTTCTTTTCT | 64 |

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference:

U.S. Pat. No. 5,378,619
U.S. Pat. No. 5,463,175
U.S. Pat. No. 5,500,365
U.S. Pat. No. 5,563,055
U.S. Pat. No. 5,633,435
U.S. Pat. No. 5,689,052
U.S. Pat. No. 5,880,275
U.S. Pat. No. 6,806,399
An et al., *Plant Physiol.*, 88:547, 1988.
Bernacchi et al., *Theor. Appl. Genet.*, 97:381-397, 1998a.
Bernacchi et al., *Theor. Appl. Genet.*, 97:170-180, 1998b.
Bird et al., *Biotech. Gen. Engin. Rev.*, 9:207, 1991.
Broothaerts et al., *Nature* 433:629-633, 2005.
Bustos et al., *Plant Cell*, 1:839, 1989.
Callis et al., *Plant Physiol.*, 88:965, 1988.
Choi et al., *Plant Cell Rep.*, 13: 344-348, 1994.
Dekeyser et al., *Plant Cell*, 2:591, 1990.
Elliott et al., *Plant Cell Rep.*, 18:707-714, 2004.
Ellul et al., *Theor. Appl. Genet.*, 107:462-469, 2003.
EP 534 858
Fraley et al., *Bio/Technology*, 3:629-635, 1985.
Fridman et al., *PNAS*, 97(9):4718-4723, 2000
Fromm et al., *Nature*, 312:791-793, 1986.
Fromm et al., *Plant Cell*, 1:977, 1989.
Fulton et al., *Theor. Appl. Genet.*, 95:881-894, 2002
Gibson and Shillito, *Mol. Biotech.*, 7:125, 1997
Jansen, *Genetics* 135:205-211, 1993.
Jansen, *Genetics* 138:871-881, 1994.
Konieczny and Ausubel, *Plant J.* 4:403-410, 1993.
Klee et al., *Bio-Technology*, 3(7):637-642, 1985.
Kuhlemeier et al., *Plant Cell*, 1:471, 1989.
Malundo et al., *Postharvest Biology and Technology* 6:103-110, 1995
Marcotte et al., *Nature*, 335:454, 1988.
Marcotte et al., *Plant Cell*, 1:969, 1989.
Monforte and Tanksley, *Genome*, 43:803, 2000.
Odel et al., *Nature*, 313:810, 1985.
Omirulleh et al., *Plant Mol. Biol.*, 21(3):415-428, 1993.
Potrykus et al., *Mol. Gen. Genet.*, 199:183-188, 1985.
Roshal et al., *EMBO J.*, 6:1155, 1987.
Schaffner and Sheen, *Plant Cell*, 3:997, 1991.
Schernthaner et al., *EMBO J.*, 7:1249, 1988.
Siebertz et al., *Plant Cell*, 1:961, 1989.
Simpson et al., *EMBO J.*, 4:2723, 1985.
Tanksley and Nelson, *Theor. Appl. Genet.*, 92:191-203, 1996
Terada and Shimamoto, *Mol. Gen. Genet.*, 220:389, 1990.
Uchimiya et al., *Mol. Gen. Genet.*, 204:204, 1986.
Wang et al., *Science*, 280:1077-1082, 1998.
Williams et al., *Nucleic Acids Res.*, 1 8:6531-6535, 1990.
WO 99/31248
Yates et al., *Euphytica*, 135:283-296, 2004

What is claimed is:

1. A tomato plant comprising a hir4 allele of *Lycopersicon hirsutum* conferring elevated Brix relative to a *Lycopersicon esculentum* plant lacking said hir4 allele, wherein the plant lacks an allele genetically linked to the hir4 allele of *Lycopersicon hirsutum* conferring increased plant vegetative growth relative to a *Lycopersicon esculentum* plant lacking said allele genetically linked to the hir4 allele, wherein said hir4 allele and allele genetically linked to the hir4 allele are located in a genomic region corresponding to markers TG155 and TG500, wherein the hir4 allele is located proximal to TG155 in said region relative to the allele conferring increased vegetative growth.

2. A plant part of the tomato plant of claim 1 wherein the plant part comprises a cell of said plant.

3. The plant part of claim 2, wherein the part is a cell, a seed, a root, a stem, a leaf, a fruit, a flower, or pollen wherein said part comprises said hir4 allele of *Lycopersicon hirsutum* and lacks said allele genetically linked to said hir4 allele conferring increased plant vegetative growth.

4. A seed that produces the plant of claim 1.

* * * * *